US008889408B2

(12) United States Patent
Mizutani et al.

(10) Patent No.: US 8,889,408 B2

(45) Date of Patent: Nov. 18, 2014

(54) FACTOR TAKING PART IN TRANSCRIPTION CONTROL

(75) Inventors: Shuki Mizutani, Chiba (JP); Takayuki Yamada, Chiba (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/296,878

(22) Filed: Nov. 15, 2011

(65) Prior Publication Data

US 2012/0088301 A1 Apr. 12, 2012

Related U.S. Application Data

(62) Division of application No. 10/522,277, filed as application No. PCT/JP03/09443 on Jul. 25, 2003, now abandoned.

(30) Foreign Application Priority Data

Jul. 25, 2002 (JP) ................................ 2002-217233

(51) Int. Cl.
*C12N 15/85* (2006.01)
*C12N 15/11* (2006.01)
*C07K 14/47* (2006.01)

(52) U.S. Cl.
USPC ...... 435/320.1; 536/23.1; 536/23.5; 435/325; 530/350

(58) Field of Classification Search
None
See application file for complete search history.

(56) References Cited

U.S. PATENT DOCUMENTS

2005/0048623 A1 3/2005 Hillman et al.
2005/0069986 A1 3/2005 Mizutani et al.

FOREIGN PATENT DOCUMENTS

WO WO 99/58559 11/1999
WO WO 00/58473 10/2000
WO WO 01/07471 2/2001
WO WO 01/60855 8/2001
WO WO 01/64834 9/2001

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Altschul, S. et al., "Basic Local Alignment Search Tool," J. Mol Biol. 215: 403-410 (1990).
Avantaggiati, M.L. et al.; "Recruitment of p300/CBP in p53-Dependent Signal Pathways," Cell 89:1175-1184 (1997).
Baniahmad, A., et al., "A transferable silencing domain is present in the thyroid hormone receptor, in the v-erbA oncongene product and in the retinoic acid receptor," EMBO Journal, 11(3), 1015-23 (1992).
Baudino, T.A., et al., "Isolation and Characterization of a Novel Coactivator Protein, NCoA-62, Involved in Vitamin D-mediated Transcription," J. Biol Chem 273(26), 16434-41 (1998).
Borrow, J. et al.,; "The Translocation t(8;16)(p11;p13) of Acute Myeloid Leukaemia Fuses A Putative Acetyltransferase to the CREB-Binding Protein," Nature Genet., 14:33-41 (1996).
Bowie et al Science, 247:1306-1310 (1990).
Chaffanet, M. et al., "MOZ Is Fused to p300 in an Acute Monocytic Leukemia With t(8;22)," Genes Chromosomes Cancer, 28:138-144 (2000).
Elbashir SM., et al. "Duplexes of 21-Nucleotide RNAs Mediate RNA Interference in Cultured Mammalian Cells," Nature, 411: 494-498 (2001).
Fan, S.J., et al. "p53 Gene Mutations Are Associated With Decreased Sensitivity of Human Lymphoma Cells to DNA Damaging Agents," Cancer Res., 54: 5824-5830 (1994).
Fondell, J.D., et al., "Unliganded thyroid hormone receptor inhibits formation of a functional preinitiation complex: implications for active repression," Genes & Develop., 7(7), 1400-10 (1993).
Fujiwara, et al. "Induction of Chemosensitivity in Human Lung Cancer Cells in Vivo by Adenovirus-mediated Transfer of the Wild-Type p53 Gene," Cancer Res., 54, 2287-2291 (1994).
Gayther, S.A. et al., "Mutations Truncating the EP300 Acetylase in Human Cancers," Nature Genet., 24:300-303 (2000).
Guo et al., "Protein Tolerance to Random Amino Acid Change," PNAS vol. 101, (25), pp. 9205-9210 (2004).
Hacia et al., Nature Genetics 22:164 (1999).
Hirososawa et al "Title" DNA Research, 6:329-336 (1999).
Ida, K. et al., "Adenoviral E1A-Associated Protein p300 Is Involved in Acute Mayeloid Leukemia With t(11;22)(q23;q13)," Blood, 90:4699-4704 (1997).
Karlin and Altschul, Proc. Natl. Acad. Sci. USA 90:5873 (1993).
Karlin and Altschul Proc. Natl. Acad. Sci. USA 87:2264 (1990).
Kitabayashi, I., et al., "Fusion of MOZ Histone Acetyltransferases in Acute Monocytic Leukemia With A t(8;22)(p11;q13) Chromosome Translocation," Leukemia, 15:89-94 (2001).
Laboratory Manual for Genetic Engineering, 3rd compiled by M. Maturura, issued by Maruzen Co., Ltd., pp. 242-246 (1996).
Lamb, J.R., et al., "Tetratrico peptide repeat interactions: to TPR or not to TPR?," Trends Biochem Sci 20(7), 257-9 (1995).
Lesk et al., Prediction of Protein Function from Protein Sequence and Structure, pp. 27-28, downloaded Sep. 17, 2007.
Lill, N.L. et al. "Binding and Modulation of p53 by p300/CBP Coactivators," Nature 387:823-827 (1997).
Lowe, S.W., et al.; "p53-Dependent Apoptosis Modulates the Cytotoxicity of Anticancer Agents," Cell 74: 954-967 (1993).
Lowe, S.W., et al; "p53 Status and the Efficacy of Cancer Therapy in Vivo," Science 266: 807-810 (1994).

(Continued)

*Primary Examiner* — Maria Marvich

(74) *Attorney, Agent, or Firm* — Finnegan Henderson Farabow Garrett & Dunner LLP

(57) ABSTRACT

HDART binds with HDAC (histone deacetylase) and functions as a repressor. HDART directly binds with Skip, which functions as a transcription co-activator of nuclear receptors, to repress the transcription by the nuclear receptor. Moreover, HDART is a transcription co-repressor of nuclear receptors, and binds with HDAC wherein transcription can be strongly repressed through the histone deacetylization of HDAC. On the other hand, a dominant negative peptide of HDART can be obtained, and it has been confirmed that, in contrast with the full-length HDART protein, this peptide activates transcription. In particular, the ability of this peptide to activate transcription by the retinoic acid receptor exceeds that of all-trans retinoic acid (ATRA).

9 Claims, 12 Drawing Sheets

(56) References Cited

OTHER PUBLICATIONS

Macdonald, P.N., et al., "Vitamin D receptor and nuclear receptor coactivators: crucial interactions in vitamin D-mediated transcription," Steroids 66(3-5), 171-6 (2001).
Molecular Cloning 3rd Ed, Chapter 2, pp. 2.1-2.117 (2001).
Molecular Cloning 3rd Ed, Chapter 8, pp. 8.1-8.126 (2001).
Nakatsu, et al., "XAB2, a Novel Tetratricopeptide Repeat Protein Involved in Transcription-coupled DNA Repair and Transcription," Journal Biological Chem., 275:34931-34937 (2000).
Hacia et al. Nature Genetics (1999)22: 164.
Niitsu, Y et al., "Cancer Gene Therapy," Molecular Medicine 35:1385-1395 (1998).
Niles R.M. Nutrition 16(11-12): 1084-9 (2000).
Noda K. et al., "Gan to kagaku chiryou hou (Cancer and its chemical therapy)," 21:1633 (1994); "Etoposide 21".
Ogawa I. et al., "Gan to kagaku chiryou hou (Cancer and its chemical therapy)", 10:2403 (1983); "VP-16-213 Phase I Study".
Okuno, M. et al., Front Biosci 7, 204-18 (2002).
Panagopoulos, I. et al., "Fusion of the MORF and CBP Genes in Acute Myeloid Leukemia With the t(10;16)(q22;p13)," Hum. Mol. Genet., 10:395-404 (2001).
Patel, et al. Biotechnology Letters, 24: 657-62 (2002).
Smith et al. "The tetratricopeptide repeats of Ssn6 interact with the homeo domain of alpha 2," Genes Dev. 9:2903-10. (1995).
Riecken E.O. and Rosewicz S. 10 Suppl 4, 197-200 (1999).
Satake, N. et al., "Novel MLL-CBP Fusion Transcript in Therapy-Related Chronic Myelomonocytic Leukemia With A t(11;16)(q23;p13) Chromosome Translocation," Genes Chromosomes Cancer, 20:60-63 (1997).
Schmutzler C. and Kohrle J. Thyroid 10(5), 393-406 (2000).
Scolnick, D.M. et al., "CREB-Binding Protein and p300/CBP-Associated Factor Are Transcriptional Coactivators of the p53 Tumor Suppressor Protein," Cancer Res., 57:3693-3696 (1997).
Seo S et al Regulation of Histone Acetylation and Transcription by INHAT, a Human Cellular Complex Containing the Set Ocoprotein, Cell, 104:119-30 (2001).
Shikama, N. et al., "A Novel Cofactor for p300 That Regulates the p53 Response," Mol. Cell, 4:365-376 (1999).
Sobulo, O.M. et al., "MLL Is Fused to CBP, A Histone Acetyltransferase, In Therapy-Related Acute Myeloid Leukemia With a t(11;16)(q23;p13.3)," Proc. Natl. Acad. Sci. USA, 94:8732-8737 (1997).
Taki, T. et al.;"The t(11;16)(q23;p13) Translocation in Myelodysplastic Syndrome Fuses the MLL Gene to the CBP Gene," Blood, 89:3945-3950 (1997).
Yang et al., "Recruitment of O-GicNAc Transferase toPromoters by Corepressor mSin3A: Coupling Protein O-GlcNacylation to Transcriptional Repression," Cell, vol. 110, pp. 69-80, (2002).
Nakatsu et al., "XAB2, a Novel Tetratricopeptide Repeat Protein Involved in Transcription-Coupled DNA Repair and Transcription," Journal Biological Chem., 275: 34931-34937 (2000).
Zhang D. et. al., J, Cell Physiol 185(1), 1-20, (2000).
Zhang, K., et al., "The *crooked neck* gene of Drosophila contains a motif found in a family of yeast cell cycle genes," Genes Dev 5(6), 1080-91 (1991).
Blatch, Gregory L. et al., "The tetratricopeptide repeat: a structural motif mediating protein-protein interactions," Review articles: *BioEssays* 21:932-939, 1999 John Wiley & Sons, Inc.

* cited by examiner

FIG. 2

```
Score = 75.5 bits(184),Expect = 3e-12
 Identities = 134/589(22%),Positives = 228/589(37%),Gaps = 127/589(21%)

 HDART: 262 LADYYIRSGHFEKARDVYEEAIRTVMTVRDFTQVFDSYAQFEESMIAAKMETASELGREE 321
            L DY +R       R +E+  IR   TV       +  YAQ+EES+   +++ A  +
 CRN  : 208 LNDYKLRK------RKTFEDNIRKNRTV---ISNWIKYAQWEESL--KEIQRARSIYERA 256

 HDART: 322 ED----DVDLELRLARFE----QLISRRPLLLNSVLLRQNPHHVHEWHKRVALHQGRPRE 373
             D    ++ L L+ A  E    Q+   R +   ++      P     W+K    +      E
 CRN  : 257 LDVDYRNITLWLKYAEMEMKNRQVNHARNIWDRAITTL--PRVNQFWYKYTYME-----E 309

 HDART: 374 IINTYTEAVQTVDPFKATGKPHTLWVAFAKFYEDNGQLDDARVILEKATKVNFKQVDDLA 433
            ++      A Q  + +            W ++  F      ++D AR I E+      F V
 CRN  : 310 MLGNVAGARQVFERWMEWQPEEQAWHSYINFELRYKEVDRARTIYER-----FVLVHPDV 364

 HDART: 434 SVWCQCGELELRHENYDEALRLLRKATALPARRAEYFDGSEPVQNRVYKSLKVWSMLADL 493
             W +    E +H  +  A ++  +A         E+F G E +    +Y +        A
 CRN  : 365 KNWIKYARFEEKHAYFAHARKVYERAV-------EFF-GDEHMDEHLYVAF------AKF 410

 HDART: 494 EESLGTFQSTKAVYDRILDLRIA---TPQIVINYAMFLEEHKY----------------- 533
            EE+    F+  + +Y    LD RI+      ++  NY +F  E K+
 CRN  : 411 EENQKEFERVRVIYKYALD-RISKQDAQELFKNYTIF--EKKFGDRRGIEDIIVSKRRFQ 467

 HDART: 534 FEESFKA--------------------------YERGISLFKWPNVSDIWSTYLTKFI- 565
            +EE  KA                          YER I+           W  Y+  +I
 CRN  : 468 YEEEVKANPHNYDAWFDYLRLVESDAEAEAVREVYERAIANVPPIQEKRHWKRYIYLWIN 527

 HDART: 566 ----ARYGGRKLERARDLFEQALDGCPPK---YAKTLYLLYAQLE---EEWGLARHAMAV 615
                +  ER R +++ +L+  P K    +AK +++LYAQ E    +    LAR A+
 CRN  : 528 YALYEELEAKDPERTRQVYQASLELIPHKKFTFAK-MWILYAQFEIRQKNLSLARRALGT 586

 HDART: 616 YERATRAVEPAQQYDMFNIYIKRAAEIYGVTHTRGIYQKAIEVLSDEHAREMC---LRFA 672
                  ++     +  +F +YI+    ++          R +Y+K +E         E C   ++FA
 CRN  : 587 ------SIGKCPKNKLFKVYIELELQLREFDRCRKLYEKFLEF-----GPENCTSWIKFA 635

 HDART: 673 DMECKLGEIDRARAIYSFCSQICDPR--TTGAFWQTWKDFEVRHGNEDTIKEMLRIRRSV 730
            ++E   LG+IDRARAIY      I  PR        W+++  DFE+     E+T +     RR +
 CRN  : 636 ELETILGDIDRARAIYELA--ISQPRLDMPEVLWKSYIDFEIE--QEETERTRNLYRRLL 691

 HDART: 731 QATYNTQVNFMASQMLKVSGSATGTVSDLAPGQSGMDDMKLLEQRAEQL 779
            Q T + +V     +Q      SG                +         M+  E++ E+L
 CRN  : 692 QRTQHVKVWISFAQFELSSGKEGSLTKCRQIYEEANKTMRNCEEKEERL 740
```

F I G. 1 0 A
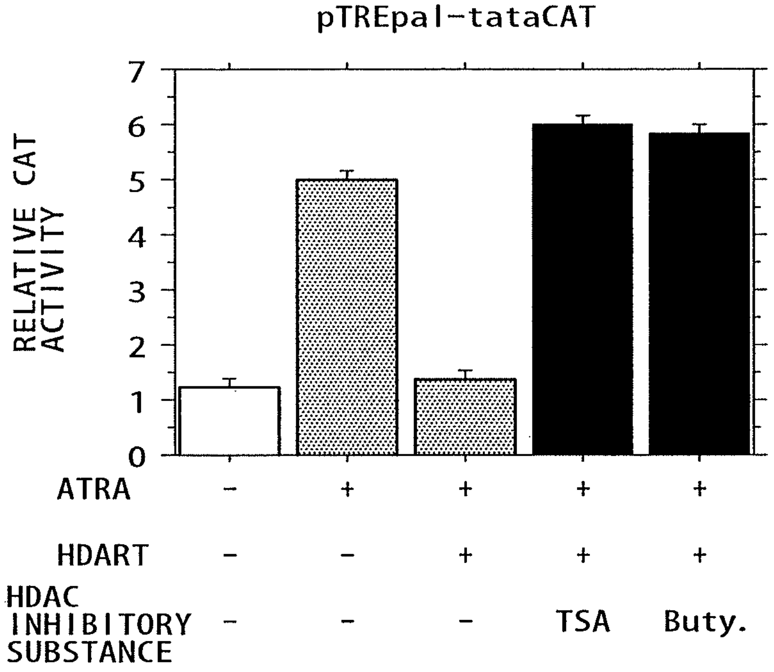
F I G. 1 0 B
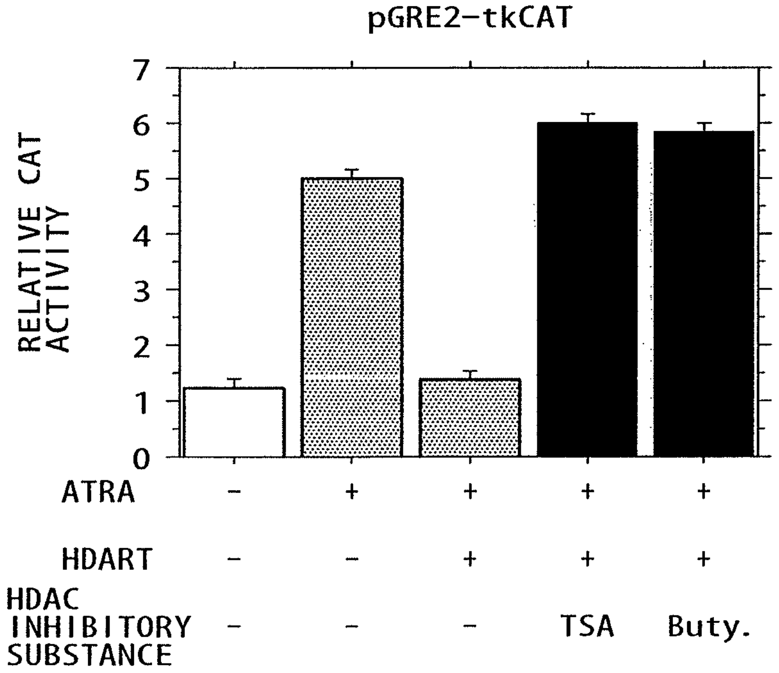

FACTOR TAKING PART IN TRANSCRIPTION CONTROL

CROSS REFERENCE OF RELATED APPLICATION

This is a divisional of application Ser. No. 10/522,277, the 371(c) date of which is Jul. 5, 2005 now abandoned, which is the U.S. National Stage of International Application No. PCT/JP03/09443, filed Jul. 25, 2003, claiming priority to Japanese Application No. JP 2002-217233, filed Jul. 25, 2002. The entire contents of all of the above applications are incorporated herein by reference.

TECHNICAL FIELD

This invention relates to transcription control factors, and more particularly, to a factor or a peptide capable of controlling the transcription mediated by nuclear hormone receptors.

BACKGROUND ART

Hormones, lipid soluble vitamins and the like play an important role in homoestatic maintenance, energy metabolism, differentiation, and growth of organisms. Transcription control factors are receptors for such hormones and reside in nuclei where they bind with particular sites of chromatin DNA to control the transcription reaction of genes. In most cases, when ligands such as a hormone are not bound with a receptor, transcription is repressed from occurring. Once a ligand, such as a hormone, binds to a receptor, the transcription is activated through a change in the chromatin structure. It has been reported that many factors called co-activators and co-repressors work by forming complexes along the pathway leading from nuclear receptors to the transcription apparatus (transcriptor). When a co-repressor complex containing a histone deacetylase binds with a receptor that is itself not bound to a ligand, gene expression is repressed. On the other hand, when the receptor structure is changed upon binding by a ligand, the co-repressor complex is released and, instead, a co-activator complex containing a histone acetylase is recruited. Mention is made, as an instance of such a co-activator, of Skip (i.e. Ski interacting protein, and also called N-CoA62), which can directly bind to several types of nuclear receptors (e.g. vitamin 3 receptor, retinoic acid receptor, estrogen receptor and glucomulticoid receptor) to strengthen the gene expression mediated by these nuclear receptors (Baudino, T. A., Kraichely, D. M., Jefcoat, S. C., Jr., Winchester, S. K., Partridge, N. C., and MacDonaldo, P. N. (1998) J. Biol. Chem. 273(26), 16434-41, MacDonald, P. N., Baudio, T. A., Tokumaru, H., Dowd, D. R., and Zhang, C. (2001) Steroids 66(3-5), 171-6).

DISCLOSURE OF INVENTION

As stated above, although the overall scheme of the transcription control mechanism as mediated by nuclear receptors continues to become more and more clear, the factors that participate in the mechanism remain to be elucidated. Therefore, one object of the invention is to provide a transcription control factor, and particularly, a novel factor that is able to take part in the transcription control by nuclear receptors.

The inventors have made studies on cloning of a human homolog of *Drosophila* crn (crooked neck) gene and also on functional analyses thereof, through which it was found that the human homolog takes part in transcription control through the nuclear receptor. It will be noted that the *Drosophila* crn gene itself is a gene that reaches a maximum level of expression in the early embryonic stage. It has been reported that the inactivation of this gene causes defects of embryogenesis and mainly influences the development of the nervous system (Zhang, K., Smouse, D., and Perrimon, N. (1991) Genes Dev 5(6), 1080-91). One specific characteristic of crn protein is that 16 copies of a longitudinally directed tetratricopeptide repeat (TRP) exist. TRP has been found in various proteins and is a degenerate 34 amino acid repeat motif that has been spread in the course of evolution. The processes in which TPR protein takes part include cell cycle control, transcription repression, stress response, protein kinase repression, and protein transport (Lamb, J. R., Tugendreich, S., and Hieter, P. (1995) Trends Biochem. Sci. 20(7), 257-9).

Like the above-indicated *Drosophila* crn gene, although the copy number, 15, is different, a number of TPR's exist in the human homolog of the crn gene. The human crn gene which has been cloned by us matches a gene (Yoshimichi et al., Journal. Biol. Chem. 275:34931-34937) coding a protein (XAB2) that takes part in transcription coupled DNA repair related to the hitherto reported transcription. Nevertheless, we have newly discovered that the product from this gene takes part in transcription repression. Especially, because the gene product functions as a repressor after binding with HDAC (histone deacetylase), we refer to it herein as "HDART" (a HDAC associated repressor TRP) protein. Moreover, we have found that HDART directly binds to Skip, the aforementioned transcription co-activator of nuclear receptors, and serves to repress the transcription by the nuclear receptor. In addition, it has also been found that HDART is a transcription co-repressor of nuclear receptors, and binds with HDAC so that it is able to strongly suppress the transcription through the histone deacetylation of HDAC. On the other hand, a dominant negative peptide has been identified and it was confirmed that, unlike full-length HDART, this peptide serves to activate transcription. Accordingly, the invention is based on newly discovered, various functions of HDART and is directed to those particularly recited below.

(1) The invention is directed to DNA coding a transcription repressing factor, including (A) DNA coding a protein having an amino acid sequence of SEQ ID NO: 2 or (B) DNA consisting of a base sequence SEQ ID NO: 1.

(2) The invention is directed to DNA coding a transcription repressing factor, including (A) DNA coding a protein having such an amino acid sequence that one or more amino acids are substituted, deleted from, inserted into and/or added to the amino acid sequence of SEQ ID NO: 2 or (B) DNA that hybridizes under stringent conditions with DNA consisting of the base sequence SEQ ID NO: 1.

(3) The invention is directed to a transcription repressing factor coded by the DNA recited in (1) or (2) above.

(4) The invention is directed to a transcription repressing factor recited in (3) above that is capable of repressing the transcription mediated by nuclear hormone receptors.

(5) The invention is directed to DNA coding a peptide capable of activating transcription, including (A) DNA coding a peptide consisting of the amino acid sequence from position 1 to 179 of SEQ ID NO: 2 or (B) DNA consisting of a base sequence from position 1 to 537 of SEQ ID NO: 1.

(6) The invention is directed to DNA coding a peptide capable of activating transcription, including (A) DNA coding a peptide having an amino acid sequence wherein one or more amino acids are substituted, deleted from, inserted into and/or added to the amino acid sequence of position 1 to 179 of SEQ ID NO: 2, or (B) DNA that hybridizes under stringent conditions with DNA consisting of the base sequence of position 1 to 537 of SEQ ID NO: 1.

(7) The invention is directed to a transcription activating peptide coded by the DNA recited in (5) or (6) above.

(8) The invention is directed to DNA that is at least a 15 nucleotide length of any one of the DNAs recited in (1), (2), (5) or (6) above.

(9) The invention is directed to a vector inserted with the DNA recited in any one of (1), (2), (5) or (6).

(10) The invention is directed to a host cell containing DNA recited in any one of (1), (2), (5) or (6) above or the vector recited in (9) above.

(11) The invention is directed to an antibody capable of binding the factor recited in (3) above or the peptide recited in (7) above.

(12) The invention is directed to an oligonucleotide probe that is hybridized with the DNA recited in any one of (1), (2), (5) or (6) and that is at least 10 nucleotides in length.

(13) The invention is directed to a substrate fixed with any of the following (A) to (D).

(A) The oligonucleotide probe recited in (12) above.

(B) The transcription repressing factor recited in (3) or (4) above or the partial peptide thereof.

(C) The transcription activating peptide recited in (7) above, or the partial peptide thereof.

(D) The antibody recited in (11) above. Below, the embodiments of the invention are described in more detail. The abbreviations used in this specification are: HAT (histone acetyltransferase or histone acetylase); HDAC (histone deacetylase or histone deacetylizing enzyme); DAPI (4',6-diamidino-2-phenylindole); RAR (retinoic acid receptor); GR (glucocorticoid receptor); DBD (DNA-binding domain); AD (activated domain); and ATRA (all-trans retinoic acid).

The invention covers factors related to transcription control. These transcription control factors include a transcription repressing factor and an activating factor. First, the transcription repressing factor is described. An instance of the transcription repressing factor of the invention includes HDART whose amino acid sequence is one indicated in SEQ ID NO: 2. It should be noted, however, that the transcription repressing factor according to the invention is not limited to the HDART indicated in SEQ ID NO: 2, but encompasses, within a range as exhibiting transcription repressing activity, proteins having such an amino acid sequence that one or more amino acids are substituted, deleted from, inserted into and/or added to the amino acid sequence indicated in SEQ ID NO: 2, and also proteins coded by DNA that hybridizes under stringent conditions with DNA coding HDART (SEQ ID NO: 1).

The HDART protein is expressed within nuclei of human cells and thus can be obtained from the nuclei of human cells. The source of human cells is not particularly limited, but by way of example mention is made, of 293 cells which are known to endogenously express HDART and so may be used.

The preparation of proteins similar to HDART, which have amino acid substitutions and the like, can be carried out by using, for example, known techniques such as a phage library screening technique (Molecular Cloning 3rd Ed, Chapter 2, pp. 2.1-2.117), and polymerase chain reaction (PCR: Molecular Cloning 3rd Ed, Chapter 8, pp. 8.1-8.126) technique. More particularly, such a protein is obtained by using DNA (SEQ ID NO: 1) coding HDART or part thereof as a probe or primer to obtain DNA homologous to SEQ ID NO: 1, followed by producing a protein based on the DNA. Typically there is high homology between HDART and the amino acid sequence. This high homology means the base sequences match at at least 40% or more, preferably, 60% or more, more preferably 80% or more, further more preferably 90% or more, still further preferably 95% or more and most preferably at least 97% or more (e.g. from 98 to 99%).

The "stringent hybridization conditions" are ones that can be appropriately selected to those skilled in the art. For instance, mention is made of hybridization which is carried out by performing pre-hybridization in a hybridization solution containing 25% formamide, or, even more stringent, 50% formamide, 4×SSC, 50 mM Hepes pH of 7.0, 10×Denhardt's solution, and 20 μg/ml of denatured salmon sperm at 42° C. overnight, adding a labeled probe to the solution, and incubating at 42° C. overnight. The wash solution and temperature conditions for subsequent washing include 1×SSC, 0.1% SDS at about 37° C., more stringent conditions include 0.5×SSC, 0.1% SDS at about 42° C., and even more stringent conditions include 0.2×SSC, 0.1% SDS at about 65° C. The combinations of SSC, SDS and temperature are mentioned for illustration only, and may be appropriately changed by those skilled in the art.

The homology of sequence can be determined by utilizing the program (Altschul et al. J. Mol. Biol, 215:403-420, 1990) of BLASTn (nucleic acid level) or BLASTx (amino acid level). The program is based on the algorithm BLAST of Karlin and Altschul (Proc. Natl. Acad. Sci. USA 87:2264-2268, 1990, Proc. Natl. Acad. Sci. USA 90:5873-5877, 1993). Where a base sequence is analyzed based on BLASTN, parameters are, for example, such that score=100 and wordlength=12. On the other hand, where an amino acid sequence is analyzed based on BLASTX, parameters are, for example, such that score=50 and wordlength=3. Where an amino acid sequence is analyzed using Gapped BLAST programs, the analysis can be carried out in a manner as described by Altschul et al. (Nucleic. Acids. Res. 25:3389-3402, 1997). When using BLAST and Gapped BLAST programs, default parameters of the respective programs are used. The specific procedures of these analyses are known in the art. Additional information is available from the National Center for Biotechnology Information and through their website.

In case where the sequence of SEQ ID NO: 2 is artificially modified, it is considered that the modification is generally less than 10% of the total amino acid residues, preferably less than 5% of the total amino acid residues and more preferably less than 1% of the total amino acid residues. As long as it is within a range where the transcription repression activity is maintained, the amino acid sequence may be substituted to such an extent exceeding the above-indicated percentage of modification. This technique of artificially modifying the amino acid sequence can be carried out, for example, by known procedures including a deletion-mutant preparation procedure, a PCR procedure, site-directed mutagenesis and the like. It will be noted that whether or not a protein modified in this way has transcription repression activity like HDART can be determined by use of many reporter analyzing methods described in examples appearing hereinafter to analyze the transcription repressing ability.

Because HDART and proteins similar thereto have such transcription repressing activity as set out above, this function may be utilized to repress the transcription of a desired gene through combination with a desired transcriptor. The transcriptor may be either an in vitro transcription system or an vivo transcription system. Since the transcription repressability of HDART is autonomous, the transcription inhibitor of the invention is able to repress transcription when used alone. In this connection, however, HDART has no ability to bind DNA and should preferably be used as a fusion protein fused with a DNA-binding region. HDART has the ability to bind HDAC and thus is able to recruit HDAC and thereby strongly repress transcription through histone deacetylase activity. Accordingly, the transcription repressing factor of the invention be used together with HDAC or by inducing HDAC to effect the repression of transcription. It is known that HDAC has type I (HDAC1, HDAC2, HDAC3) and type II (HDAC4, HDAC5, HDAC6, HDAC7, HDAC8). The HDART of the invention is considered to bind to HDAC2, HDAC5, HDAC7, HDAC8 and the like. Thus, in the practice of the invention, HDAC2, HDAC5, HDAC7, and HDACB can be conveniently used. However, limitation should not be placed on the use of these HDAC5 alone, but HDAC5 belonging to either of type I or II may also be usable.

Since HDART is able to repress nuclear receptor transcription, a transcriptor working through a nuclear receptor is a suitable example of a transcriptor capable of being repressed by means of the transcription repressing factor of the invention. Suitable examples of the nuclear receptor are retinoic acid receptor and glucocorticoid receptor. Moreover, nuclear receptors for hormones and fat-soluble vitamins, such as retinoid X receptor, vitamin D receptor, androgen receptor, estrogen receptor, thyroid hormone receptor and the like, may also be included within the scope of factors that repress transcription according to the invention. Hence, the transcription repressing factor of the invention is useful for treating diseases caused by the unregulated transcription from such nuclear receptors, particularly, by the excess promotion of the transcription. Especially, as is shown in examples appearing below, because it has been found that HDART represses the transcription of retinoic acid receptor and also inhibits the differentiation induced by the transcription of the retinoic acid receptor, the transcription repressing factor of the invention may be applied as a therapeutic medicine against diseases that are ascribed to increased differentiation based on the transcription by the retinoic acid receptor.

The invention relates to DNA encoding the transcription repressing factor. For example, such DNA may be DNA consisting of the base sequence indicated in SEQ ID NO: 1, however DNA is not limited thereto. The DNA also includes DNA that codes the amino acid sequence indicated in SEQ ID NO: 2, DNA coding a protein having an amino acid sequence wherein one or more amino acids are substituted, deleted from, inserted into and/or added to the amino acid sequence indicated in SEQ ID NO: 2, and DNA that hybridizes with DNA consisting of the base sequence indicated in SEQ ID NO: 1 under stringent conditions.

The above DNA can be obtained from, for example, a cDNA library of human cells (e.g. island cells of the human pancreas as shown in Example 1 appearing hereinafter are mentioned) by using DNA of SEQ ID NO: 1 or part thereof as a probe or primer for hybridization or polymerase chain reaction (PCR). Alternatively, as another method, the DNA may also be obtained by RT-PCR (Molecular Cloning 3rd Ed, Chapter 8, Protocol 8, pp. 8.46-8.53) wherein mRNA of the human cells is used as a template and a part of the DNA of SEQ ID NO: 1 is used as a primer. It will be noted that although the use of the human cells has been illustrated above, the preparation may be carried out using, aside therefrom, other mammalian cells, eukaryotic cells and the like. In addition, the hybridization conditions for isolating DNA are those indicated above.

Aside from the above-stated procedure of cloning the DNA, the DNA may be prepared by synthesizing DNA of SEQ ID NO: 1 and the complementary strand, respectively, by use of a DNA synthesizer, followed by annealing the two.

The above DNA codes the transcription repressing factor and can thus be used as a tool for producing the transcription repressing factor or as a tool for expressing the transcription repressing factor in cells or individuals. When used for this purpose, it is preferred to incorporate the DNA into an expression vector or the like. The type of expression vector can be appropriately selected depending on the translation system used in the production of protein or the cell to be used.

For the production of the transcription repressing factor using the DNA-incorporated vector, the vector is first introduced into host cells, and the host cells are cultured. In this way, the transcription repressing factor is produced in the host cells. The procedure of introducing the vector into the cells may be appropriately selected depending on the type of cell used. For instance, there may be used a virus vector or phage-mediated biological technique, chemical techniques such as a calcium phosphate method, a lipofection method and the like, physical techniques such as a gene gun method and an electroporation method, and the like. The protein produced in the host cell can be purified (e.g. by affinity purification), if necessary, and then used.

The DNA-incorporated expression vector may also be used for the purpose of repressing a desired transcription within the cells or within an individual. More particularly, when the expression vector is introduced into the cells or an individual and expresses the transcription repressing factor, the desired transcription system can be repressed. In particular, because HDART has autonomous transcription repression ability, even when used alone the transcription repressing factor of the invention shows transcription repressing activity. However, because HDART itself does not bind to DNA, it is preferred that this transcription repressing factor is expressed as a fusion protein with a DNA binding region capable of binding on DNA of a control region of a desired gene. In doing so, the transcription of a target gene can be repressed. The transcription repressing factor of the invention can bind to HDAC, so that when the transcription repressing factor is expressed, HDAC is recruited, and transcription is repressed more intensely.

Because the transcription repressing factor encoded by the DNA according to the invention has the capability of effectively repressing the transcription by nuclear receptors, the vector incorporated with this DNA may be applied as a composition for treating diseases ascribed to the increased transcription by these nuclear receptors. As for vectors for intended treatments, mention is made, for example, of virus vectors such as retrovirus vector, adenovirus vector, adeno-associated virus vector, vaccinia virus vector, lenti virus vector, herpes virus vector, alpha virus vector, EB virus vector, papillomavirus vector, foamy virus vector and the like.

Among the transcription control factors of the invention, and contrary to those noted above, are peptides that are capable of activating transcription. The full length HDART functions as a transcription repressing factor. On the contrary, a dominant negative peptide of HDART functions as a transcription activator. Examples of the dominant negative peptide include a peptide coded with four TPR's (hereinafter abbreviated as "N4TPR") at the N terminus, i.e., a peptide consisting of an amino acid sequence from position 1 to position 179 in SEQ ID NO: 2, although not limited thereto. Provided that transcription activity is possessed, those peptides wherein one or plural amino acids are substituted with, deleted from, inserted into and/or added to the amino acid sequence from position 1 to position 179 in SEQ ID NO: 2 may also be included.

The dominant negative peptide can be prepared by synthesizing a peptide based on DNA consisting of a base sequence from 1 to 537 of SEQ ID NO: 1. Moreover, the synthesis of peptides having, for example, a substituted amino acid sequence can be carried out based on DNA wherein codons are changed by adding a variation (substitution, deletion, insertion and/or addition) to the base sequence in positions 1 to 537 of SEQ ID NO: 1.

The above peptide has transcription activation activity and can be used to promote the transcription of desired transcription systems. Especially, as shown in examples, because N4TPR of HDART activates the transcription by nuclear receptors, it may be used to promote the transcription by these nuclear receptors. For the nuclear receptor, mention is favorably made of nuclear receptors on which Skip acts, e.g. retinoic acid receptor, glucocorticoid receptor, vitamin D receptor, estrogen receptor, and the like. And, to the extent that the peptides of the invention activate their transcription, nuclear receptors against hormones or fat-soluble vitamins, such as retinoid X receptor, androgen receptor, thyroid hormone receptor and the like, may also be included.

It is shown in examples appearing below that the transcription activation activity of retinoic acid receptor by the action of the N4TPR is higher than the transcription activation activity caused by ATRA. Hence, a differentiation-inducing therapy of malignancies such as leukemia is now carried out through the transcription activation activity of retinoic acid receptor promoted by means of ATRA. Moreover, vitamin A, and derivatives thereof including ATRA have started to be used for treating, aside from leukemia, hepatic cell carcinoma (Okuno, M. et al., (2002) Front. Biosci. 7, 204-18), ovarian cancer (Zhang D. et. al., (2000) J. Cell Physiol. 185(1), 1-20), thyroid cancer (Schmutzler C. and Kohrle J. (2000) Thyroid 10(5), 393-406), skin cancer (Niles R. M. (2000) Nutrition 16(11-12), 1084-9), pancreatic cancer (Riecken E. O. and Rosewicz S. (1999) 10 Suppl 4, 197-200) and the like. The peptide of the invention may be used instead of, or in combination with ATRA.

The invention also relates to DNA coding a peptide having such transcription activation activity as stated above. More specifically, such DNA is DNA coding a peptide consisting of an amino acid sequence from 1 to 179 of SEQ ID NO: 2, one examples of which includes DNA consisting of a base sequence made of bases of Sequence Nos. 1 to 537. Not limited thereto, there may also be included, so far as they have transcription activation activity, DNA coding a peptide having an amino acid sequence wherein one or more amino acids are substituted with, deleted from, inserted into and/or added to an amino acid sequence from 1 to 179 of SEQ ID NO: 2, and DNA that hybridizes under stringent conditions to DNA consisting of a base sequence of bases 1 to 537 in SEQ ID NO: 1.

DNA coding the transcription-activating peptide can be prepared by first obtaining the aforementioned DNA coding the transcription repressing factor and, for example, causing deletion of the C terminus side. Alternatively, the DNA may be prepared by synthesis using a DNA synthesizer.

The DNA can be used for the purpose of producing the transcription-activating peptide or can be introduced into cells or individuals to express therein the transcription-activating peptide. Where the DNA is used for producing a peptide, it is preferred to incorporate it in an expression vector. In this case, the expression vector can be appropriately selected depending on the transcription/translation system for producing a peptide. This transcription/translation system may be either in vitro or in vivo. With the in vivo system, the expression vector incorporated with the DNA is introduced into cells and the cells are cultured, and the transcription-activating peptide is produced within the cell. Methods for introducing into cells are similar to those stated above.

Where the DNA is used for the purpose of expressing the transcription activated peptide after introduction into cells or individuals, the DNA may be directly introduced into cells or the like for transient expression or inserted in chromosomes for stable expression, or may be incorporated into an expression vector and introduced into cells or the like.

As stated above, like ATRA, the transcription-activating peptide may be applied to differentiation-inducing therapy of malignancy, and thus can be utilized for the therapy wherein instead of directly using the transcription-activating peptide, this DNA is, e.g., injected into a patient to cause expression of the transcription-activating peptide. To this end, it is preferred to use the DNA incorporated into a vector for carrying the DNA to the desired tissue or cells. Regarding vectors useful for this type of therapy, a virus vector such as the afore-indicated retrovirus vector or the like may be used.

As stated above, by shortening the DNA at the N-terminal side of the transcription repressing factor coded by the DNA of the invention, it may be modified into DNA coding the transcription-activating peptide. In addition, the DNA coding the transcription repressing factor or the DNA coding the transcription-activating peptide can, when provided as a shorter fragment, be used as a probe for hybridization, a PCR primer or a ribozyme derivative. When such fragments of the above-mentioned DNA are used for this purpose, it is preferred that the fragment is of a length that retains specificity for its use as a probe or the like, for example, a 15 nucleotide length. The invention provides oligonucleotide probes that are at least 10 nucleotides in length, and hybridize with the DNA of the invention (e.g. DNA indicated at SEQ ID NO: 1 or the like). For instance, such a polynucleotide includes those which specifically hybridize to DNA consisting of the base sequence indicated in SEQ ID NO: 1 or the complement thereof. The term “specifically hybridized” used herein means that in hybridization, there is no significant cross-hybridization with DNA that codes for a different protein. The above-mentioned probe and primer can be used for cloning or the like of DNA coding a transcription repressing factor or the like.

The invention also relates to an antibody capable of binding to the transcription repressing factor or transcription-activating peptide. The antibody of the invention may be either a polyclonal antibody or a monoclonal antibody provided that it specifically binds to the transcription repressing factor or transcription-activating peptide. The polyclonal antibody can be prepared by using the protein of the invention or a partial peptide thereof, and, if necessary, mixing with Freund’s adjuvant, immunizing a nonhuman animal such as rabbit, goat, guinea pig or the like according to known procedures, and collecting serum from the peripheral blood of the immunized animal after confirming increased antibody level. On the other hand, the monoclonal antibody is prepared by immunizing an animal such as mouse according to known procedures using the transcription repressing factor, transcription-activating peptide or a partial peptide thereof, removing the spleen or the lymph nodes from the immunized animal whose antibody level has increased, and creating a fusion of antibody-producing cells and myeloma cells to prepare a hybridoma. Thereafter, antibody produced from the hybridoma is collected from the culture supernatant liquid to obtain the monoclonal antibody.

These antibodies can be utilized not only for affinity purification of the transcription repressing factor or transcription-activating peptide, but also for the immunological analysis of the amount of expression of the transcription repressing factor in various cells or for inhibiting the transcription repressing factor.

Also, the invention provides a substrate with the aforementioned oligonucleotide immobilized thereon. Using the substrate as a biochip, one may, for example, analyze the expression levels in a test organism (cells) of DNA of the invention.

In a preferred embodiment, DNA of the invention (e.g. DNA indicated in SEQ ID NO: 1 or a partial DNA region thereof) from a test organism (cells) is amplified. Next, a substrate having immobilized thereon a nucleotide probe that hybridizes with said DNA is provided. Thereafter, said DNA and said substrate are brought into contact with each other. Then, by detecting the DNA that hybridized with the nucleotide probe fixed on the substrate, the expressed levels of the DNA of the invention can be analyzed.

Such a method includes, for example, a DNA array technique. The preparation of a DNA sample from a test organism (cells) can be performed by procedures known to those of the skill in the art. In a preferred embodiment of preparing the DNA sample, the preparation is possible using chromosomal DNA extracted from the cells. For the preparation of the DNA sample for this procedure using chromosomal DNA, for example, employing a primer that hybridizes with the DNA of the invention, it is possible to prepare the DNA of the invention by PCR or the like using the chromosomal DNA as a template. The thus prepared DNA sample may be labeled for detection by methods known in the art, if necessary.

The term "substrate" used in this invention means a planar-shaped material to which nucleotides can be immobilized thereon, and, is commonly referred to as a chip. In the practice of the invention, the term nucleotide includes oligonucleotide and polynucleotide. Although the substrate of the invention is not critical, so long as nucleotides can be immobilized thereon, substrates ordinarily used in the DNA array technique are favorably used.

In general, the DNA array is composed of several thousands of nucleotides printed on a substrate at high density. Usually, these DNA's are printed on the surface layer of a non-porous substrate. The surface layer of the substrate is usually glass, but a porous membrane such as, for example, a nitrocellulose membrane may be used.

In the practice of the invention, oligonucleotide arrays as developed by Affymetrix Inc., are exemplified as the method for immobilizing (array) nucleotides. For oligonucleotide arrays, the oligonucleotide is typically synthesized in situ. For instance, the in-situ synthetic methods of oligonucleotides have been already known including, for example, a photolithographic technique (Affymetrix Inc.), an ink-jet technique (Rosetta Inpharmatics LLC Co.) of fixing chemical substances, and the like. All of these techniques can be utilized for the fabrication of the substrate of the invention.

The type of nucleotide probe immobilized on the substrate is not critical provided that the DNA of the invention is able to be detected therewith. More particularly, the probe is, for example, one that specifically hybridizes with the DNA indicated at SEQ ID NO: 1. As long as specific hybridization is possible, the nucleotide probe does not have to be fully complementary to the DNA of the invention.

According to the invention, the length of the nucleotide bound on the substrate is, in the case of immobilized oligonucleotides, generally 10 to 100 bases, preferably 10 to 50 bases, and more preferably 15 to 25 bases.

In the practice of the invention, the DNA sample and the substrate are then brought into contact with each other. According to this procedure, the DNA sample is hybridized with the nucleotide probe. The reaction solution and reaction conditions for the hybridization may change depending on the factors including the length of nucleotide to be fixed on the substrate and the like, but generally the method can be conducted by procedures well known to those of the skill in the art.

Next, according to the invention, the presence or absence, or the intensity of the hybridization between the DNA sample and the nucleotide probe fixed on the substrate is detected. This detection can be carried out by reading, for example, a fluorescent signal such as by a scanner or the like. It will be noted that with respect to DNA arrays, it is usual to refer to the DNA fixed on the slide glass as probe and labeled DNA in the solution as target. Accordingly, the nucleotide immobilized on the substrate is set forth as nucleotide probe in this specification. In the above procedure, the thus detected hybridization intensity is compared with a control, if necessary. For the procedure, mention is made, for example, of a DNA array method (Strategies of SNP Gene Variation, by Kenichi Matsubara and Yosiyuki Sakaki, published by Nakayama Shoten, p. 128-135; Nature Genetics (1999)22: 164-167) and the like, which can be appropriately carried out by those skilled in the art with reference to the literature.

In addition, the invention provides a substrate, on which the protein of the invention or a partial fragment of the protein is immobilized. When using said substrate as a biochip, it becomes possible to search for molecules that bind to the protein of the invention, or to screen for HDAC inhibitor compounds and the like.

In general, substrates with proteins fixed thereon are called protein chips. Like DNA chips, the principle is such that proteins are fixed on a slide glass or membrane in high density, and protein or nucleic acids that interact therewith are detected.

Because the HDART protein of the invention binds with various types of HDAC proteins, it can be applied to the screening of HDAC inhibitor compounds. More particularly, the fixing of the HDART protein of the invention on a solid phase surface permits different types of HDAC's to be bound on one surface. When different types of compounds are bound on this solid phase surface and HDAC activities are measured, HDAC inhibitor compounds can be screened.

An example of an HDAC inhibitor compound obtained by the above screening method includes tricostatin A, a medicine used in differentiation-inducing therapy of cancer.

Also, substrates with antibodies of the invention immobilized thereon can be used as a biochip. Immobilization, on the chip surface, of isolated, highly purified antibodies enables one to achieve high densification.

In a preferred embodiment of the invention, after spotting a sample onto a substrate, by rinsing the substrate proteins which do not show any affinity for the spotted surface or other foreign matters are washed away. A subsequent detection step can be performed by those of skill in the art according to an appropriate, known method while taking into account the type of substrate and the like, thereby detecting the presence or absence (or strength) of affinity. As one example, energy absorbing molecules (EAM) are added to the above-mentioned substrate after the rinsing step and, after drying, subjected to a mass spectrometer (TOF-MS) device to measure molecular weight spectra of proteins bound to the spotted surface.

The immobilization of an arbitrary DNA or peptide to a substrate can be conveniently carried out by those skilled in the art according to known procedures.

BRIEF DESCRIPTION OF DRAWINGS

FIG. 2 is a view comparing the CRN homology region between the human HDART (SEQ ID NO: 3) and the human CRN (SEQ ID NO: 4).

FIG. 4A shows the results of analysis of the interaction between the foreign HDART and foreign Skip. Lane 1 is for GFP-HDART alone, lane 4 is for Flag-Skip alone, and lanes 2, 3 are for both expressed within 293 cells. Lane 5 is for control cells free of any vector. Lanes 1, 2, 4 and 5 are, respectively, directed to samples immunoprecipitated with an anti-Flag antibody, and lane 3 is directed to a sample immunoprecipitated with control mouse IgG. The upper two panels show the expression of the expressed proteins, and the lower two panels show immunoprecipitates, respectively. It will be noted that the upper panels show the results immunoblotted with an anti-GFP antibody and the lower panels show the results immunoblotted with an anti-Flag antibody.

FIG. 4B shows the results of analyses of the interaction between the internal HDART and the foreign Skip. After introduction of Flag-Skip (lane 1) or Flag-luciferase (lane 2) into 293 cells internally holding HDART, the cell extract was immunoprecipitated with an anti-Flag antibody. A control test where no vector was introduced was also run in parallel (lane 3). The expression state of the HDART protein within cells (upper panel), immunoprecipitated Flag (central panel) or the HDART (lower panel) was identified by immunoblotting using an antibody indicated at the left of the panel as "WE".

FIG. 5A shows mapping of HDART-binding region sites on Skip. The plus (+) sign shows that the interaction is detected based on β-galactosidase activity in a yeast two-hybrid system. The number of the pluses indicates the relative intensity of the interaction. NHR binding: nuclear hormone receptor bound domain, TA: trans activated domain.

FIG. 5B shows the mapping of the Skip-binding region on the HDART. The symbols are the same as defined above.

FIG. 6A shows the results of repression which depends on the concentration of HDART with respect to the transcription activated by means of retinoic acid. The CAT activity shown has been corrected relative to the CAT activity determined for a system with a vacant vector (1.0 μg) in the absence of a ligand. An average of three replicated measurements is shown with the error bar indicating S.D.

FIG. 6B shows the results of repression which depends on the concentration of HDART with respect to the transcription undergoing the activation with glucocorticoid.

FIG. 7A shows the localization of endogenous HDART protein. The left side panels show the results of immunofluorescent staining using an anti-HDART antibody (upper side) or preimmune serum (lower side), and the right side panels show the results of DAPI staining in fields corresponding to the left side panels.

FIG. 7B shows the localization of HDART in viable cells. The results of observation of fluorescence caused by GFP after introduction of a GFP-HDART expression vector (upper left) or a GFP expression vector (lower left) into Hela cells, and the results of visualized the nucleus using the Hoechst 33342 dye (upper right) are shown.

FIG. 8A shows the results of study of the promoter repression activity when different amounts of Gal4 DBD HDART expression plasmid (0, 0.1, 0.3, 0.5 μg) are introduced into Gal4 reporter (luciferase) plasmid-bearing NIH3T3 cells. The corrected luciferase value relative to the luciferase activity (100%) obtained on introduction of a vacant vector alone is shown. An average of the results of three replicated experiments is shown, and an error bar indicates S.D.

FIG. 8B shows the results using U-20S cells.

FIG. 9A shows the interaction between HDART and HDAC. The results of immune blotting with an antibody (anti-Flag antibody or anti-GFP antibody) immunoprecipitated and labeled with an anti-FLAG antibody after co-transfection of a GFP-HDART expression vector and a FLAG-HDACs expression vector ((lane 1, HDAC1; lane 3, HDAC3; lane 4, HDAC4; lane 5, HDAC6) into 293 cells (at the central and lower panels, respectively). It will be noted that lane 2 is for a sample wherein GFP-HDART alone is introduced. The upper panel shows the results of confirmation of the expression of GFP-HDART protein using a sample prior to immunoprecipitation.

FIG. 9B shows the results of the direct interaction of HDART and HDAC3.

FIGS. 10A to 10B show the inhibition of HDART repressions with two types of HDAC inhibitory substances (tricostatin A, sodium butyrate), respectively (C, D).

FIG. 11A shows the inhibition of the N4TPR-mediated interaction of endogenous HDART and Skip. The results of a test wherein a cell extract of 293 cells subjected to transfection of Flag-Skip and GFP (lane 1) or GFP-N4TRP (lane 2) was immunoprecipitated with an anti-Flag antibody and the resultant precipitated product was isolated with SDS-Page are shown. The lower three panels, respectively, show immunoprecipitated Skip (upper panel) endogenous HDART (middle panel) and N4TPR (lower panel). The expression of HDART protein prior to the immunoprecipitation is shown at the uppermost panel.

FIG. 11B is a graph showing the activation of the transcription ascribed to the retinoic acid receptor by the action of N4TPR.

FIG. 11C is a graph showing the activation of the transcription ascribed to glucocorticoid receptor by the action of N4TPR.

FIG. 12A is an ATRA (−) and vacant vector-introduced sample, FIG. 12B is an ATRA (+) and vacant vector-introduced sample, FIG. 12C is an ATRA (−) and HDART expressed vector, FIG. 12D is an ATRA (+) and HDART expressed vector, FIG. 12E is a phase contrast photograph in the same field of view as FIG. 12C, and FIG. 12F is a phase contrast photograph in the same field of view as FIG. 12D. In FIG. 12F, the black arrow indicates an undifferentiated GFP positive cell, and a white arrow indicates a differentiated GFP positive cell. In FIG. 12G, the graph shows a percentage of morphologically differentiated cells in the GFP positive cells. The results of four independent experiments are submitted as an average and S. D. (error bar) (P<1% between Mock and HDART at ATRA(+), Student's t-test).

BEST MODE FOR CARRYING OUT THE INVENTION

The invention is described in detail by way of working examples, which should not be construed as limiting the invention thereto.

Example 1

Cloning of Human HDART

Figure 1:
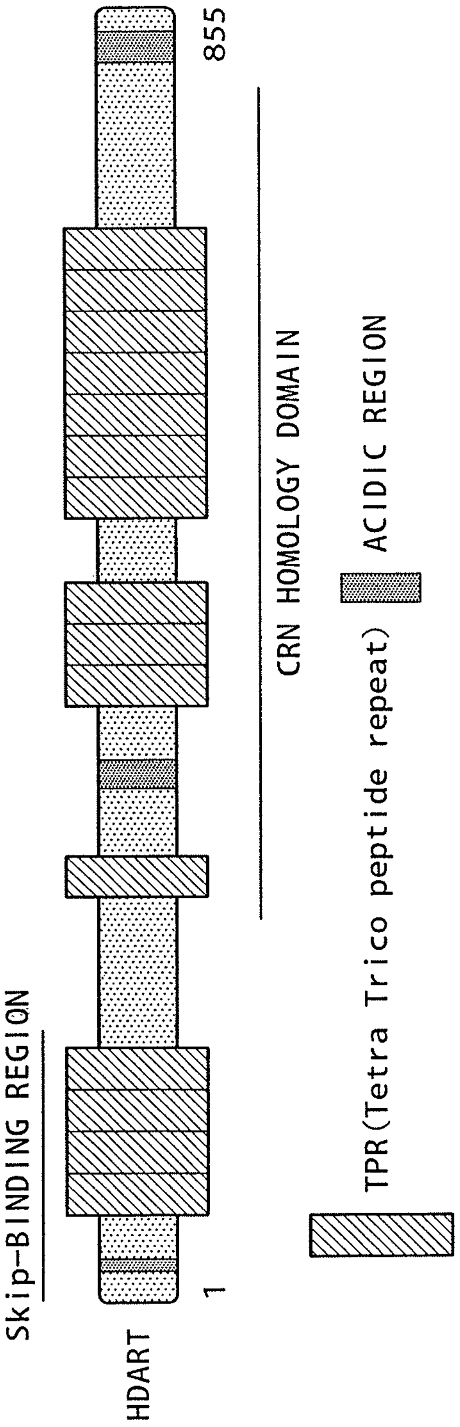
FIG. 1 shows that HDART is a TPR (Tetra trico peptide repeat) protein, and shows the configuration thereof and the association with related genes. A schematic configuration of the primary structure of HDART, TRP, acidic regions, a Skip interacting region, and a CRN homology region are shown.
Figure 3:
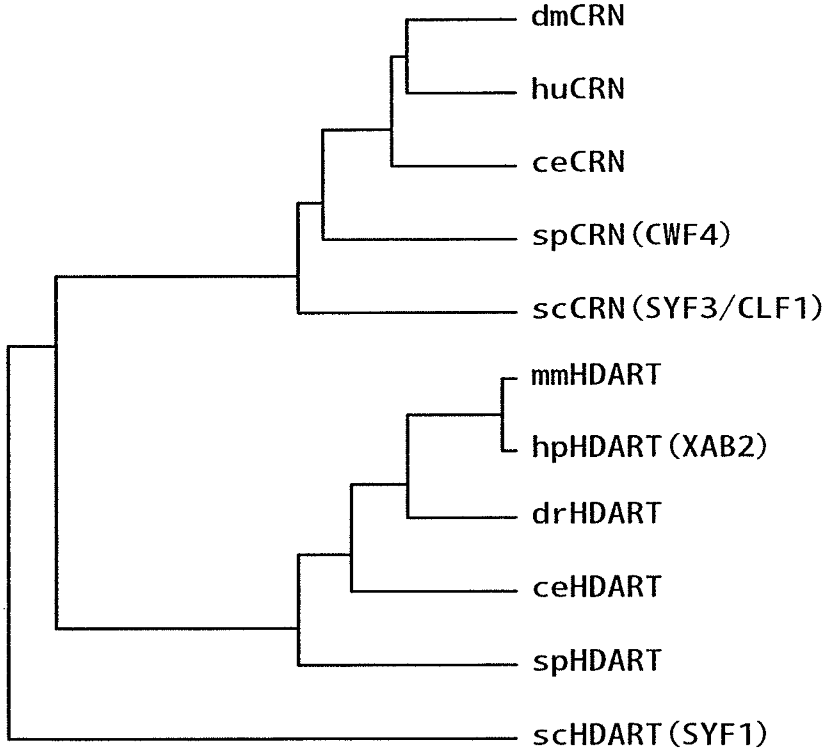
FIG. 3 is a view showing a HDART/CRN protein-protein phylogenetic tree. This phylogenetic tree was constructed with GENETYX-MAC program (development software).

A search of the BLAST database for human homologs of *Drosophila* crn gene revealed that the clone #52930 of human EST (expressed sequence tag) derived from the pancreatic islets has high homology with the ern gene. The full sequence of the clone w52930 was determined by standard methods. Moreover, using the 5'-RACE procedure (5'-rapid amplification of cDNA ends strategy), this gene was identified as having a full length of cDNA consisting of 2660 bases with one long reading frame. It will be noted that the identified protein functions as a repressor after binding to HDAC (histone deacetylase) as will be described hereinafter and thus is called "HDART (a HDAC associated repressor TPR)" protein. HDART is a 855 amino acid, highly-conservatively-coded TPR protein (FIG. 1). The HDART human protein deduced from the DNA sequence clearly indicates a resemblance to human CRN protein. Especially, the region ranging from residue 262 to residue 779 of the HDART human protein is highly conserved in the HDART and CRN protein (FIGS. 1, 2). The genetic analyses of the proteins among several species revealed that these formed a genetic family (FIG. 3).

Example 2

Direct Interaction Between HDART and Transcription Coactivator Skip

Noting that several TPR regions exist on HDART, it was examined whether there are any proteins capable of interacting with HDART via these TPRs.

In order to isolate a protein that binds to this HDART, a yeast two-hybrid system was used. More particularly, a yeast MATCHMAKER two-hybrid analysis kit (Clontech) was used for the isolation. The ORF full length of HDART was inserted so that it and the Gal4 DNA binding domain reading frame were aligned in the same frame with each other within pAS-1 vector (Clontech). This bait plasmid was transformed into *Saccharomyces cerevisiae* Y190 along with pACT2 prey plasmid whose HeLa cDNA (Clontech) had been sub-cloned. The screening for clones into which both plasmids were introduced was carried out according to the kit protocol. In this way, the results of cloning at about $1\times10^7$ lead to isolation of several clones. The analysis of these clones revealed that one matched with Skip.

The interaction between HDART and Skip inside the mammalian cells was confirmed according to the immunoprecipitation analysis. For the confirmation, the Flag-Skip expression vector expressing the Flag-Skip fused protein and the GFP-HDART expression protein expressing the GFP-HDART fused protein (FIG. 4A) were transfected into HEK293 cells by use of Effectene kit (QIAGEN™). It will be noted that a control experiment was conducted such that the Flag-Skip expression vector alone and the GFP-HDART expression vector were, respectively, transfected into cells of the same type under the same conditions.

24 hours after the transfection, the cells were lysed on ice for 30 minutes in a Nonidet P-40 buffer solution (50 mM Tris HCl (pH 7.6), 150 mM NaCl, 5 mM EDTA, 0.5% Nonidet P-40 and 1 mM PMSF) containing 100 μl of a protease inhibitory substance cocktail (Sigma #p8340) to prepare a cell extract (1 mg). This extract was incubated for 30 minutes at 4° C. along with 40 μl of protein A/G sepharose beads for preliminary clarification. Next, the thus clarified supernatant extract was further incubated for 1 hour along with an anti-Flag antibody or a negative control mouse IgG antibody (2 μg), followed by precipitation for 30 minutes by use of 40 μl of protein A/G sepharose beads. The resulting immunoprecipitate was washed four times with Nonidet P-40 buffer solution. The bound protein was dissolved out from A/G sepharose beads in an SDS loading buffer to develop the eluate with SDS-PAGE. After the development, transcription on a membrane was carried out, followed immunoblotting of the membrane in the usual manner. For an antibody of this immunoblotting, there were used anti-FLAG antibody M2 (Sigma) and anti-GFP monoclonal antibody clone 1E4 (MEL).

Figure 4B:
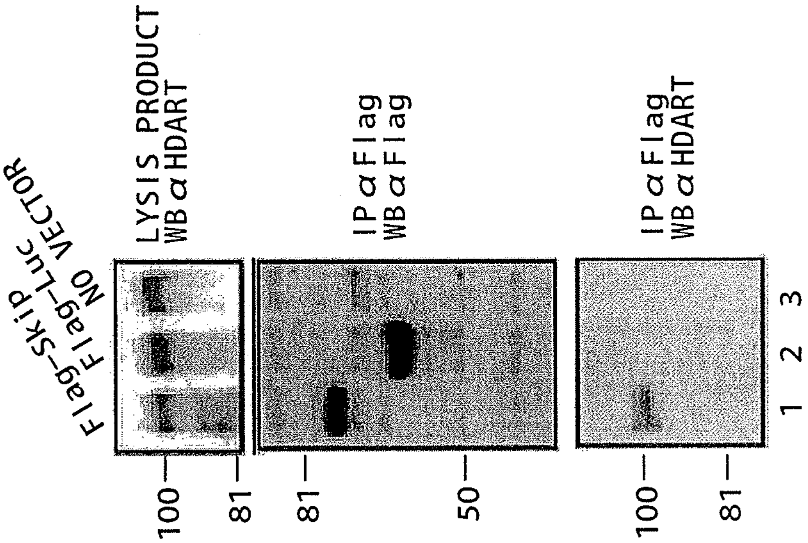
FIGS. 4A to 4B are photographs showing the results identified through immunoprecipitation analyses of the interaction between foreign or internal HDART and foreign Skip.
Figure 4A:
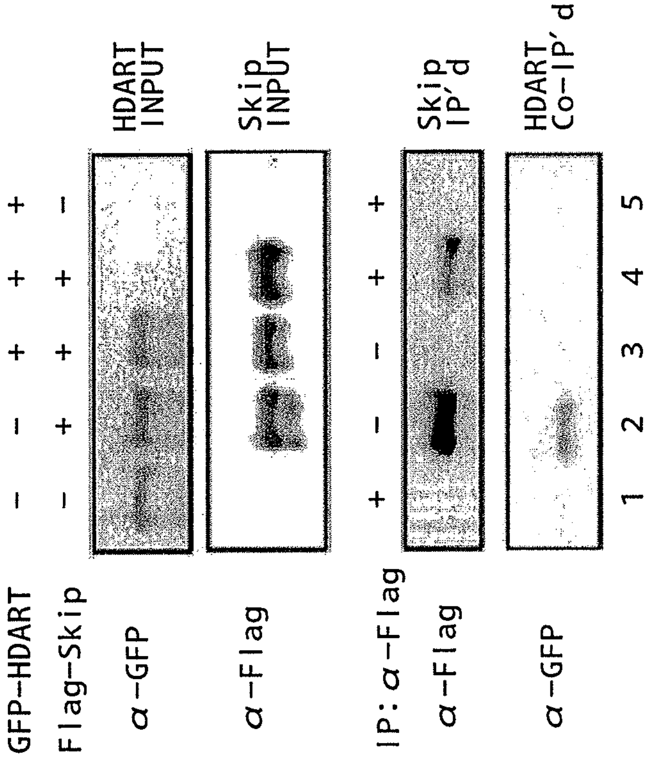

The results of the immunoprecipitation analysis are shown in FIG. 4A. In the figure, the upper two panels show the results of expression of the respective proteins, and the lower two panels show those of the immunoprecipitates. A shown in FIG. 4A, only when both composite proteins are expressed, the GFP-HDART protein was immunoprecipitated by means of the anti-Flag antibody along with the Flag-Skip fused protein (lane 2). Under conditions where no FLAG-Skip is expressed, no precipitation of GFP-HDART with the anti-FLAG antibody was observed (lane 1), no precipitation was likewise observed in the case using the negative control antibody (lane 3). These results suggest that HDART and Skip specifically interact in vivo.

Further, the interaction of endogenous HDART and externally introduced Skip was analyzed. A Flag-Skip expression vector or a Flag-luciferase expression vector was transfected into 293 cells (i.e. cells highly expressing HDART), followed by preparation of a cell extract 24 hours after the transfection in the same manner as set out above. This cell extract was incubated with an anti-Flag antibody and immunoprecipitated. The immunocomplex or cell extract prior to the immunoprecipitation was developed with SDS-PAGE, and transferred to a membrane. This membrane was immunoblotted by use of an anti-HDART antibody or an anti-Flag antibody. The results are shown in FIG. 4B. It should be noted that in FIG. 4B, the upper panel shows the results of immunoblotting of the cell extract with the anti-HDART antibody, the central panel shows the results of immunoblotting with the anti-Flag antibody after immunoprecipitation with the anti-Flag antibody, and the lower panel show the results of immunoblotting with the anti-HDART antibody after immunoprecipitation using the anti-Flag antibody.

As shown in FIG. 4B, HDART was co-precipitated by means of the anti-Flag antibody under conditions of expression of Flag-Skip only (lane 1 of FIG. 4B), and no co-precipitation was observed under conditions where the Flag-Luc protein was expressed (lane 2) and with the parent 293 clone where nothing was transfected (lane 3).

Example 3

Binding Region of HDART and Skip

Figure 5A:
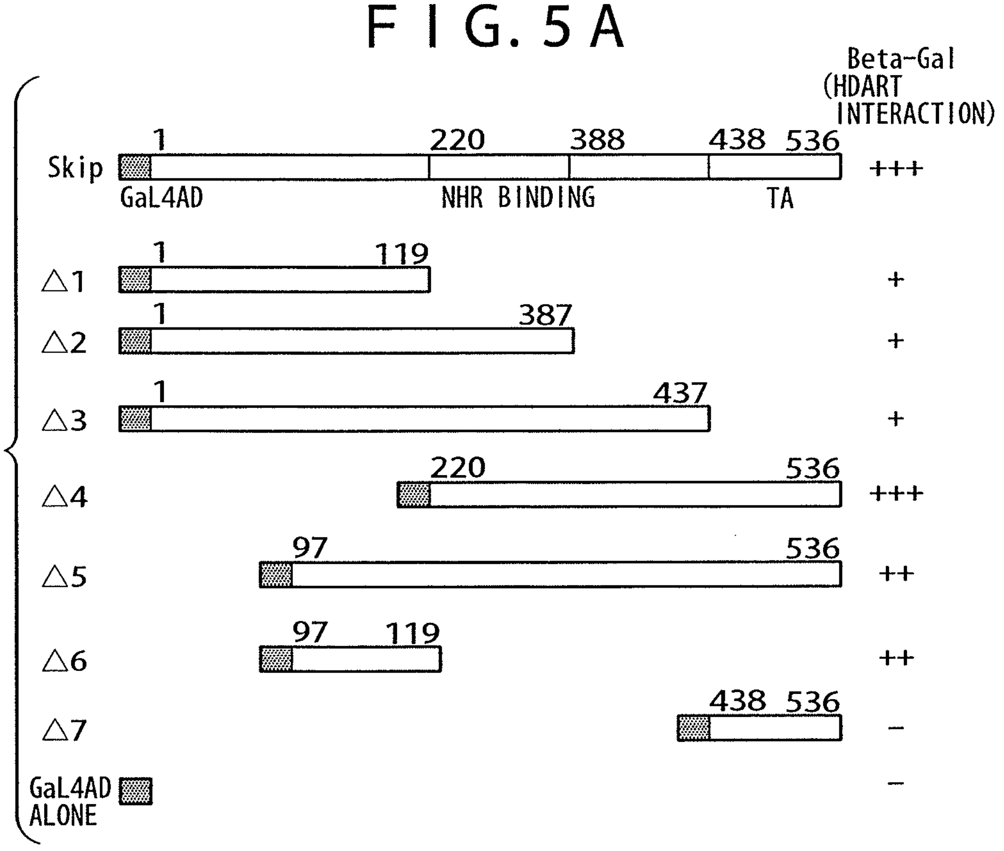
FIGS. 5A to 5B show the identified interaction regions of both Skip and HDART proteins.

For mapping of regions on the Skip taking part in the interaction with HDART, a series of deletion mutations where various regions on Skip (N-terminus region (codon 1-220), nuclear hormone binding region (NHR binding, codon 221-388), and tran-activation region (TA, codon 438-536) were deleted, and the interaction between HDART and mutated Skip was analyzed according to the yeast two-hybrid analysis using Gal4DBD-HDART as set forth in Example 2. The results of the analysis are shown in FIG. 5A. The sign "+" indicated at the right of FIG. 5A indicates the observation of the interaction by the filter lift analysis of β-galactosidase activity, and the number of "+" indicates the relative intensity of the interaction. The sign "−" indicates no detection of the interaction.

Figure 5B:
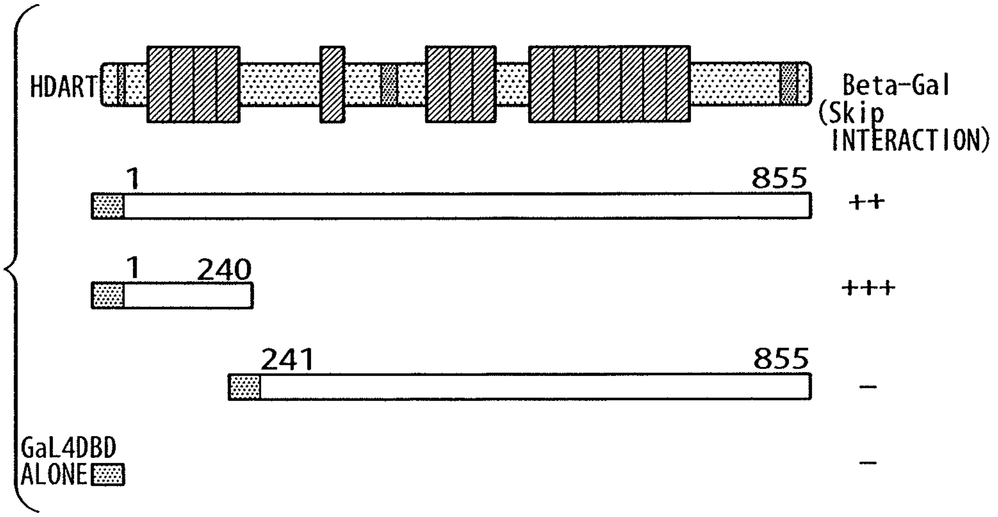

As shown in FIG. 5A, we discovered that two different regions take part in the interaction with HDART. Such regions include: one within residues 97-119 and the other within residues 220-437. It was shown that the trans-activation region of Skip scarcely takes part in the binding activity with HDART. A similar approach was carried out for analyzing the region on HDART taking part in the interaction with Skip. More particularly, various deleted allelic mutants of Gal4DBD-HDART were prepared to analyze the galactosidase upon interaction thereof with Gal4AD-Skip. The results of the analysis are shown in FIG. 5B. It was demonstrated that the N-terminus region including four TPRs (1-179 residues) ensures the interaction with Skip to a full extent (FIG. 5B). Accordingly, HDART is able to directly interact with Skip via the four TPR regions of the N-terminus.

Example 4

Inhibition of Gene Transcription Ascribed to Nuclear Receptors by HDART

Since it is shown in the above example that HDART is able to interact with Skip, the functional role of HDART on the transcription route ascribed to a nuclear receptor was analyzed. First, the effect of HDART on the transcription regulation by retinoic acid receptor was analyzed. For this purpose, the CAT analysis was made using a RAR (retinoid acid receptor) reporter plasmid incorporating a thymidine kinase minimum promoter (pTREpal-tata) and CAT gene therein downstream of a retinoid response element.

More particularly, pcDNA3-HDART, capable of steadily expressing HDART, and, at the same time, RAR reporter plasmid, were transfected into HepG2 cells by use of Effectene kit (QIAGEN™). It is to be noted that the pcDNA3-HDART expression vector was introduced in different amounts of 0, 0.5 and 1.0 μg, and the amount of DNA in the respective transfections was equalized at 1 μg by adding the appropriate amount of a vacant vector of pcDNA. After the transfection, growth was made in the presence ($10^{-8}$ M) or absence of ATRA and the CAT activity was measured. The results of the measurement (FIG. 6) are indicated in terms of values corrected on the basis of the CAT activity obtained after introduction of 1.0 μg of a vacant vector in the absence of ATRA. In addition, the average of the results of three experiments and a standard deviation in terms of an error bar are also shown.

Figure 6A:
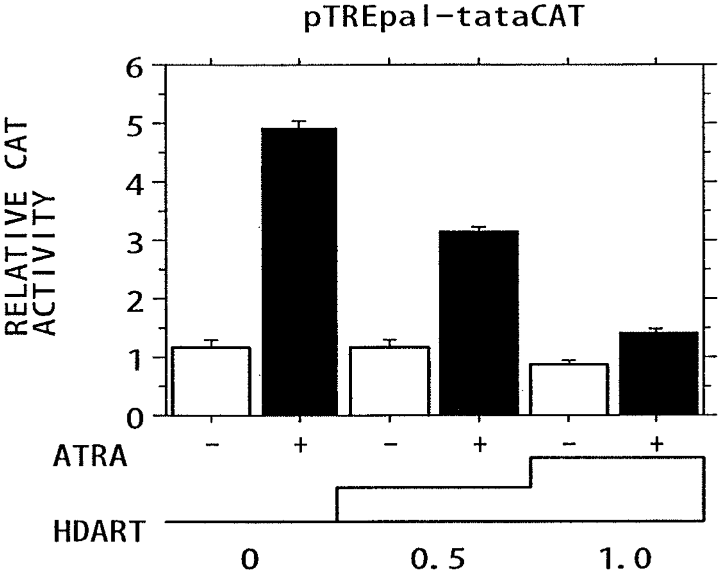
FIGS. 6A to 6B are graphs showing the repression, with HDART, of the transcription activity ascribed to the nuclear hormone (retinoic acid or glucocorticoid).

As shown in FIG. 6A, in the cells receiving the vacant vector (pcDNA), CAT activity increased five-fold in the presence of ATRA. However, this ATRA-induced CAT activity was inhibited by HDART in a concentration dependent manner.

Furthermore, the action of HDART on the transcription regulation by glucocorticoid receptor (GR) was analyzed by use of GR reporter plasmid in GR positive Hela cells. The transcription activity of a glucocorticoid response promoter was carried out in the same manner as in the experiment for the retinoic acid receptor except for the use of Hela cells and $10^{-8}$ M of dexamethasone. The results of the measurement are shown in the same manner as shown above.

Figure 6B:
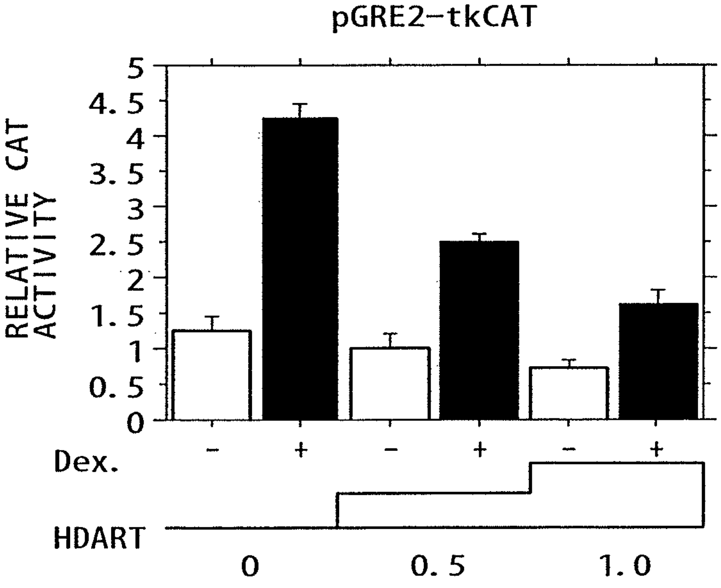

The co-expression of HDART was repressed to a similar extent as observed with the RAR (retinoic acid receptor) induced trans-activation and thus, the activation of the reporter gene responding to glucocorticoid was inhibited (FIG. 6B). These results show that HDART selectively represses the transcription activated by means of the nuclear receptor.

Example 5

Localization of HDART in Cell Nuclei

Since it is shown that HDART directly takes part in the transcription control, it is presumed that HDART is localized in nuclei of cells. Based on this, a polyclonal antibody against a HDART recombinant protein was prepared in order to analyze the localization of HDART within cells by an immunofluorescent experiment.

The preparation of the polyclonal antibody was produced in *Escherichia coli* as His-HDART (amino acid residues 296-431) fused protein, followed by purification with a Ni-NTA resin (QIAGEN™) showing affinity for His. Next, a rabbit was immunized with the His-HDART protein, and the resulting anti-HDART antiserum was further purified by affinity chromatography using Prot0n kit 1 (MPS). The thus purified rabbit anti-HDART antibody was incubated with Hela cells inherently holding HDART therein, followed by further incubation with PE (phycoerythrin) fused rabbit antibody for carrying out immunofluorescent staining. It will be noted that for a control test, a similar procedure was repeated using pre-immunization rabbit serum in place of the rabbit anti-HDART antibody. In addition, in order to clarify the location of nucleus, DAPI staining was also carried out.

Figure 7A:
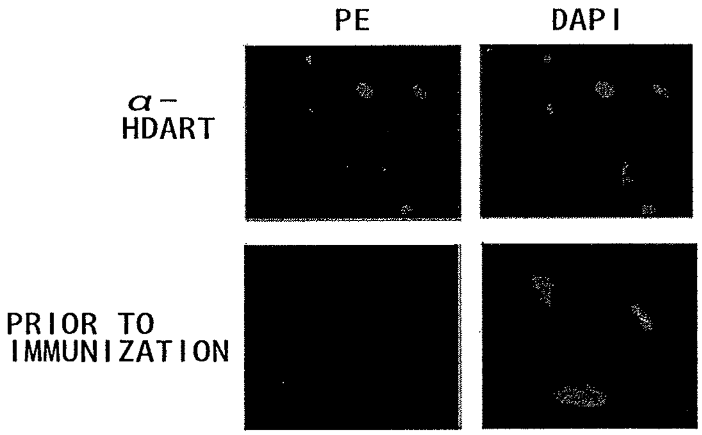
FIG. 7A to 7B are photographs showing the localization within cells of HDART.

As shown in FIG. 7A, the immunofluorescent stained image using the anti-HDART antibody coincided with the DAPI stained image. On the other hand, for the preimmune serum, the nucleus was not stained. From these results, it was shown that HDART was predominantly localized within nuclei of the Hela cells (FIG. 7).

The location of HDART in viable cells was also analyzed. A GFP or GFP-HDART expression vector was transfected into Hela cells. After 24 hours, GFP fluorescence was measured. As to the GFP-HDART cells, incubation was performed using Hoechst 33342 dye so as to visualize the nuclei.

Figure 7B:
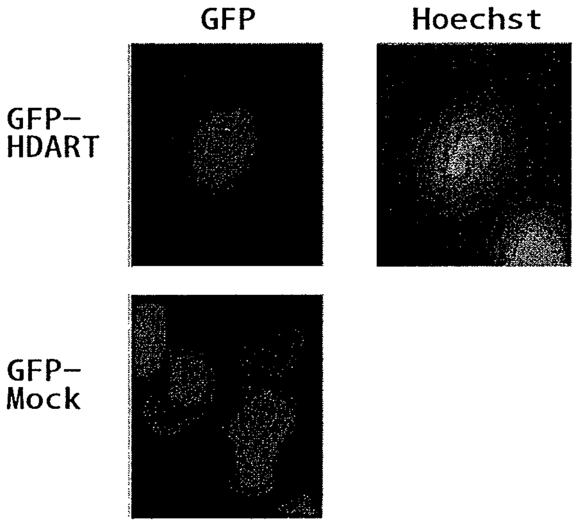

As shown in FIG. 7B, with the cells transfected with GFP-HDART vector, it was confirmed that the nuclei visualized with Hoechst 33342 dye (upper right panel) emits fluorescence with GFP (left upper panel). Especially, GFP-HDART showed a pattern partly similar to the hitherto reported nuclear speckle pattern (17) of the Skip molecule. Similar results were also observed with respect to HT1080 cells and 293 cells (not shown).

Example 6

Autonomous Repression Function Caused by HDART

Assuming that HDART takes part in more direct inhibition, it is expected that it has an autonomous repression function. To confirm the above expectation, in order that HDART can bind to DNA the full-length HDART cDNA was fused to Gal4 DNA binding region (GAL4DBD: a region having only a binding region with GAL4DNA and lacking a transcription control region) to analyze whether the transcription from the GAL4A promoter could be regulated within NIH3T3 cells.

Figures 8A, 8B:
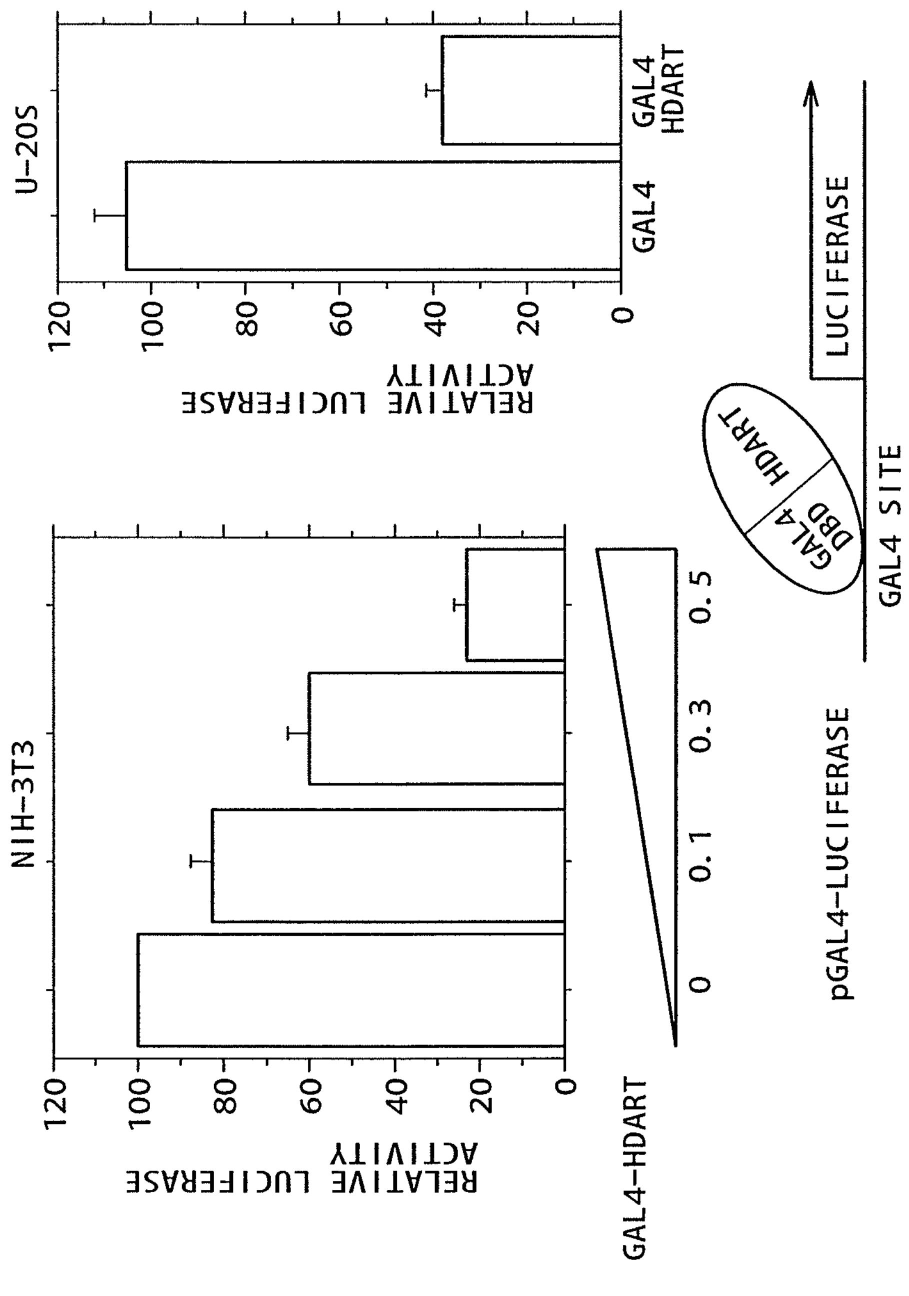
FIGS. 8A to 8B show the autonomous promoter repression activity of HDART.

More particularly, a Gal4 DBD-HDART plasmid capable of expressing a full-length HDART and Gal4 DBD fused protein was transfected in different amounts (0, 0.1, 0.3, and 0.5 μg) into NIH3T3 cells previously prepared to contain Gal4 reporter plasmid (pGal4-Luciferase). It should be noted that in order to make a uniform total amount of DNA used for the transfection, the amount of an expression vector was equalized to 0.5 μg by adding the appropriate amount of a vacant vector of Gal4 DBD in each transfection. 24 hours after the transfection, the expression activity (Luciferase activity) of reporter genes from the promoter was analyzed. The luciferase activity for each sample is indicated as a corrected value based on the luciferase activity obtained by introduction of a vacant vector alone as a reference (100%) (FIG. 8). It will be noted that the results of the analysis were indicated as an average of the results of three experiments, and a standard deviation is indicated as an error bar (FIG. 8A). Similar analyses were made using a different type of cell, U-205 cell, with Gal4 DBD-HDART (in an amount of 0 or 0.5 μg) (FIG. 8B).

HDART significantly inhibits the promoter activity within the NIH-3T3 cells in concentration-dependent manner, and lowers the expression of luciferase by 80% at the highest concentration (0.5 μg) (FIG. 8A). Similar results were observed with the case of the U-205 cell (FIG. 8B). From these results, it was shown that HDART itself possesses autonomous transcription inhibitory activity.

In the case of HDART not having a GAL4 DNA binding region, expression inhibition of luciferase was not observed (not shown). From this, it will be seen that HDART has no binding activity to the promoter region of DNA.

Example 7

Suppressing Mechanism Ascribed to HDART

It has been reported that acute transcription is regulated by the degree of acetylation of core histone, which is mediated through a mechanism involving activation by HAT (histone acetylase) and repression by HDAC (histone deacetylase). In order to elucidate the genetic repression mechanism caused by HDART, an immunoprecipitation analysis using Flag-HDAC expression vector was used to investigate whether or not HDART functions through the formation of a complex with HDAC.

Flag-HDACs expression vectors capable of expressing different types of HDAC (1, 3, 4 or 6) and a GFP-HDART expression vector were, respectively, co-transfected with 293 cells in the same manner as in Example 2, and cell extracts were prepared 24 hours after the transfection. The respective cell extracts were incubated with an anti-Flag antibody, followed by immunoprecipitation. The resulting immunoprecipitate was isolated with SDS-PAGE and an isolated pattern was transferred to a membrane, followed by immunoblotting with use of an anti-Flag antibody or anti-GET antibody. For reference, in order to confirm the expression of GFP-HDART protein in the respective cells, individual samples prior to the immunoprecipitation were similarly developed with SDS-PAGE to conduct immunoblotting with use of an anti-GFP antibody. It will be noted that in FIG. 9A, the upper panel shows the results of the expression of the GFP-HDART protein prior to the immunoprecipitation, the central panel shows the results of the immunoblotting of the immunoprecipitate with the anti-Flag antibody, and the lower panel shows the results of the immunoblotting of the immunoprecipitate with the anti-GFP antibody. The kinds of HDAC's from the left side of the figure are as follows: lane 1, HDAC1; lane 3, HDAC3; lane 4, HDAC4; and lane 5, HDAC6. It will be noted that lane 2 is for the sample in which GFP-HDART alone was expressed.

Figure 9A:
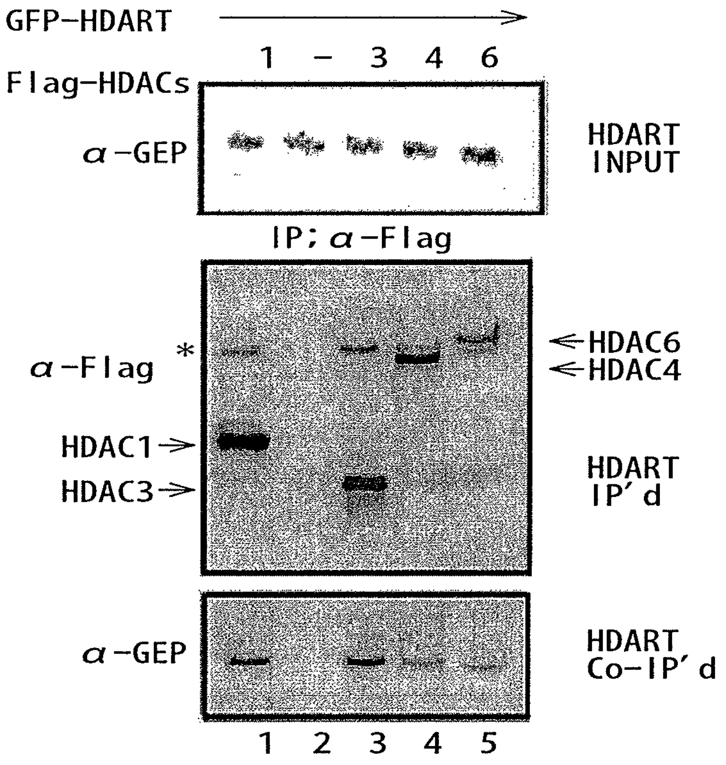
FIGS. 9A to 9B are photographs showing direct interaction between HDART and HDAC.

As shown in FIG. 9A, with a 293 cell-derived extract wherein the Flag-HDAC expression vector and the GFP-HDART expression vector were co-transfected, it was confirmed that GFP-HDART was immunoprecipitated with the anti-FLAG antibody (lower panel, lanes 1, 3, 4, 5 from the left). However, no precipitation of GFP-HDART was observed in the absence of FLAG-HDAC (a line into which no Flag-HDAC expression vector was introduced) when the anti-FLAG antibody was added (lower panel, lane 2). Accordingly, it was demonstrated that the precipitation of GFP-HDART with the anti-FLAG antibody depends on the specific interaction between Flag-HDAC and GFP-DART. Moreover, it was also shown that HDART exhibits interaction with both types of HDAC's including type I (HDAC's 1 and 3) and type II (HDAC's 4 and 6).

Further, the direct interaction between HDART and HDAC3 was investigated by GST pulldown analysis. The GST pulldown analysis was essentially carried out according to a known procedure (Tzamarias, D., and Struhl, K. (1995) Genes Dev 9(7), 821-31.). Using TNT (Registered Trademark) in vitro transcription/translation system (Promega), the in vitro translation of HDAC3 was made in the presence of $^{35}$S-methionine. GST protein or GST-HDART fused protein was, respectively, expressed within *Escherichia coli*, followed by purification in a GST binding buffer solution (50 mM tris-HCl, 200 mM LiCl, 0.5% NP40, 5 mM EDTA, 1 mM PMSF) by use of glutathione sepharose. A binding reaction solution containing GST-HDART fused protein or control GST protein (about 1 μg) and $^{35}$S-radio-labeled in vitro translation product (10 μl) in 1 ml of the GST binding buffer solution was prepared. This reaction solution was incubated at 4° C. for one hour while shaking, after which the resulting the sepharose-GST protein complex was washed five times with the GST binding buffer solution. The protein bound with the GST protein was eluted by boiling in a sodium dodecylsulfate (SDS) containing sample buffer solution, followed by isolation with SDS-polyacrylamide gel electrophoresis. It was confirmed by Coomassie brilliant blue staining that the GST fused protein was equally electrophoresed, and $^{35}$S-radio-labeled HDAC was detected according to autoradiography.

Figure 9B:
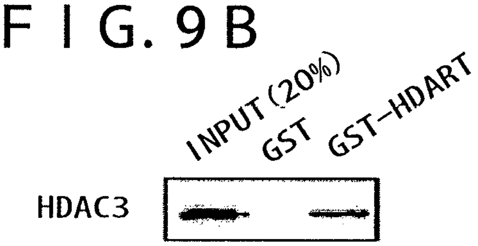

As shown in FIG. 9B, the in vitro translated HDAC3 did not bind to just GST protein and could not be pulled down. However, when using the GST-HDART fused protein, it was shown to be pulled down (FIG. 9B). Although not shown in the figure, similar results were obtained for HDAC1. From this, it was suggested that the interaction between the HDART and HDAC was direct in nature.

In order to analyze the influence of the transcription inhibition action of HDART on the deactylization activity of HDAC, CAT reporter analysis was carried out in the manner as in Example 4 in the presence of tricostatin A (TSA), which specifically inhibits HDAC (FIGS. 10C and D). In this example, however, a given amount of pcDNA3-HDART expression vector (1 μg) ("HDART+" in FIGS. 10) and 100 nM of TSA or 1 mA of sodium butyrate was added to along with a ligand (ATRA or dexamethasone).

As shown in FIGS. 10C, D, in the presence of ligand alone, expression of the reporter gene from the corresponding promoter increased, and when HDART was also expressed, the expression activity was suppressed. When triconstatin A was further added, the expression repression by HDART was fully neutralized. The same results were also observed in the case where another type of histone deacetylase inhibitor, sodium butyrate (Buty), was added. These results supported the idea that the transcription inhibition by HDART occurs via the deacetylase activity.

Example 8

Active Repression of Unliganded Receptor with HDART-Skip Interaction

RAR and TR inhibit the genetic activity in the absence of a ligand in vivo (Baniahmad, A., Kohne, A. C., and Renkawitz, R. (1992) Embo J 11(3), 1015-23) and in vitro (Fondell, J. D., Roy, A. L., and Roeder, R. G. (1993) Genes Dev 7(7B), 1400-10). From this, this is called active repression. Skip interacts with NHR independently of ligand (MacDonald, P. N., Baudino, T. A., Toumaru, H., Dowd, D. R., and Zhang, C. (2001) Steroids 66 (3-5), 171-6). In view of these repressing effects and the physiological involvement with Skip, there has been suggested the possibility that the HDART-Skip complex exists as an unliganded receptor or the possibility that the interaction takes part in the active repression of receptor. In order to clarify these possibilities, a dominant negative line of HDART is overexpressed to check the influence on the transcription ascribed to RAR. As shown in Example 2, the four TRPs (N4TPR) at the N terminus of HDART are in the Skip binding region, so that it is hypothesized that the expression of this region inhibits the interaction between the endogenous HDART and Skip, it is inhibiting the natural function of HDART and functioning as a dominant negative. In this sense, the N4TPR was used as a candidate for dominant negative in this example.

Figure 11A:
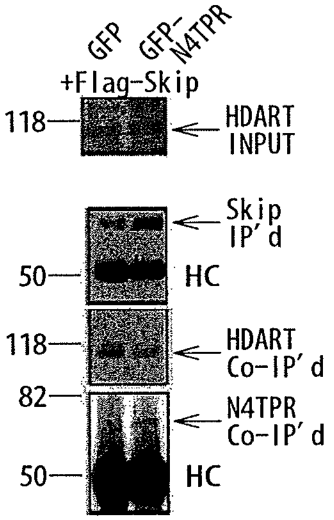
FIGS. 11A to 11C include graphs and a photograph showing dominant negative effects of four TPR's (N4TPR) at the N terminus of HDART.

Flag-Skip and N4TPR tagged with GFP or GFP were transfected into 293 cells. 24 hours after the tranfection, a cell extract was prepared, followed by immunoprecipitation with an anti-Flag antibody. The resultant immunoprecipitate was isolated on SDS-PAGE. To confirm the expression of the endogenous HDART prior to the immunoprecipitation, a cell extract prior to the immunoprecipitation was likewise isolated with SDS-PAGE. The pattern after the isolation was transferred to a membrane. The expression of Flag-Skip was detected using an anti-Flag antibody, the expression of GFP and GFP-N4TPR detected using an anti-GFP antibody, and the expression of the internal HDART detected using an anti-HDART antibody, respectively (FIG. 11A). It will be noted that in FIG. 11A, the lower three panels, respectively, show precipitated Skip (top of the lower panels), endogenous HDART (middle of the lower panels), and N4TPR (bottom of the lower panels), and one top panel shows the expression of an endogenous HDART protein prior to the immunoprecipitation.

As shown in FIG. 11A, the expression of N4TPR lead to a more reduced amount (lower center panel, lane 2) of HDART co-precipitated with Skip in comparison with a control where no N4TPR was expressed (GFP alone, lane 1). On the other hand, overexpression of N4TPR contributes to increasing the interaction between N4TPR and Skip, with a remarkable increase in amount of the co-precipitated Skip (lane 2, lower bottom panel). The expression of the control protein (GFP) exhibits no influence on the interaction between HDART and Skip (lane 1). The results show that N4TPR acts as a dominant negative protein which interacts with Skip in place of HDART.

Next, the influence of the overexpression of N4TPR on the transcription from RAR or a glucocorticoid responsive promoter was checked. It will be noted that this test was made in the same manner as in the reporter analysis set out in Example 4, but using GFP-N4TPR expression vector (0, 0.3 and 0.5 μg).

Figure 11B:
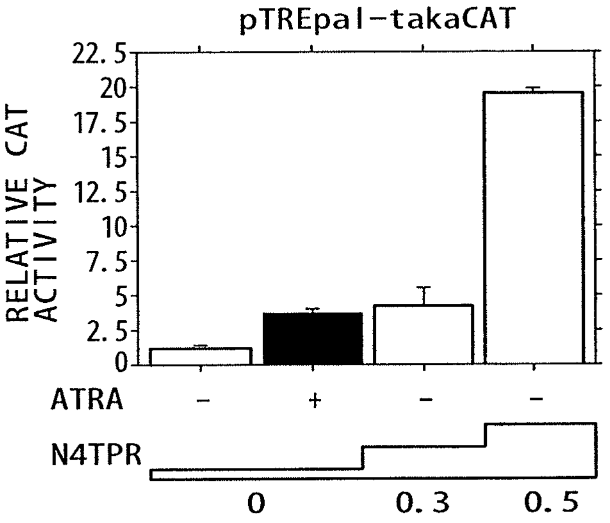
Figure 11C:
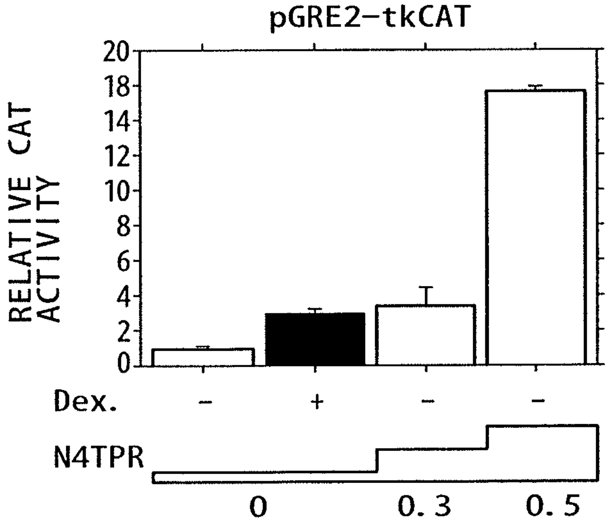

As the results in FIGS. 11B, C show, expression in the absence of ligand and with limited N4TPR (introduced amount of 0.3 μg), the degree of transcription activity from the RAR and glucocorticoid responsible promoter was increased up to the amount (gray column) of transcription activity induced by the presence of ligand. At the highest expression level (amount: 0.5 μg) of N4TPR, the transcription activity in the absence of a ligand was strongly increased (to about 20 times). These results suggest that HDART is necessary for the active repression of nuclear hormone receptors such as RAR, glucocorticoid receptor and the like.

Example 9

Inhibition, by Overexpression of HDART, of Differentiation of Rhabdomyosarcoma Cell Line into Muscle Tissue Derived from Retinoic Acid It is known that ATRA (all-trans retinoic acid) is an important inducer for tumor cell differentiation (20-22). The human rhabdomyosarcoma cell line MM-1-19-P is constituted mainly of small polygonal cells, which when provided with retinoic acid, ultimately differentiate into myotubular cytomegalic cells. In order to clarify the physiological role of HDART in the reaction ascribed to nuclear hormone receptors, the influence of the expression with HDART on the differentiation of MM-1-19-P caused by ATRA was analyzed.

MM-1-19-P cells were plated in a 100 mM Petri dish, followed by co-transfection of the cells with 0.4 μg of pGFP vector and 2 μg of pcDNA3 (vacant vector) or pcDMA3-HDART (HDART expression vector). 24 hours after the transfection, the medium was changed with an ATRA-containing (2 μM) or ATRA-free fresh one. After induction over 48 hours, at the time when the cells changed into elongated spindle cells exhibiting myotubular cytomegalic cells, the cells were assessed as having been morphologically differentiated. All experiments were repeated four times, and the number of cells assessed as positive for GFP was counted. The results are shown in FIG. 12. It will be noted that in FIG. 12, the standard microphotographs of green fluorescence of GFP are shown in panels of FIGS. 12A, 12B, 12C and 12D, and the phase differential microphotographs are shown in panels of FIGS. 12E and 12F, respectively. In the figure, 12A indicates ATRA non-treated, vacant vector-introduced cells, 12B indicates ATRA treated, vacant vector-introduced cells, 12C indicates ATRA-non-treated, HDART expression vector-introduced cells, 12D indicates ATRA-treated, HDART expression vector-introduced cells, 12E indicates cells under the same conditions as in 12C above, and 12F indicates cells under the same conditions as in 12D above. In addition, the black arrow in the panel of FIG. 12F indicates undifferentiated GFP positive cells, and white arrow indicates differentiated cells. In FIG. 12G, the graph shows the percentage of morphologically differentiated cells in the GFP positive cells as an average of the results of four independent experiments, and the standard deviation is indicated in terms of error bar (P<1% between a vacant vector/ATRA (+) and an HDART expression vector, Student's t test).

In the respective experiments, the number of GFP positive cells ranged 30 to 70. For the cells treated with the vacant vector and ATRA, the number of GFP positive cells was found to be less than 30% because of the cytotoxic effect of ATRA. On the other hand, for the HDART expression vector-introduced cells, the numbers of GFP positive cells were same for the ATRA treated group and non-treated group.

Figure 12A:
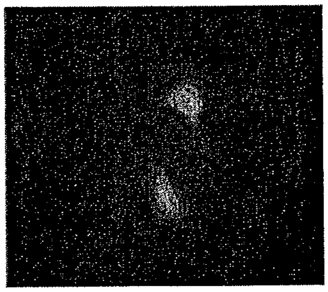
FIGS. 12A to 12G include graphs and photographs showing the inhibition, with HDART, of differential induction with retinoic acid within MM-1-19-P cells. The MM-1-19-P cells into which a HDART expression vector or a vacant vector had been introduced was analyzed with respect to the differentiation induction in the presence or absence of ATRA (2 μM) In order to identify transduced cells, a GFP vector was co-transfected along with the above-indicated vector. The photographs (12A, 12B, 12C and 12D) of green fluorescence with GFP taken through standard microphotography, and photographs (12E, 12F) taken under a phase-contrast microscope are shown.
Figure 12B:
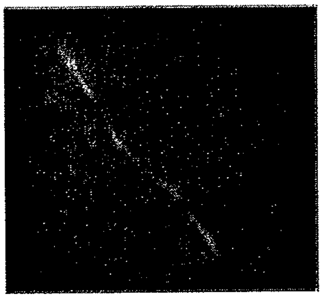
Figure 12C:
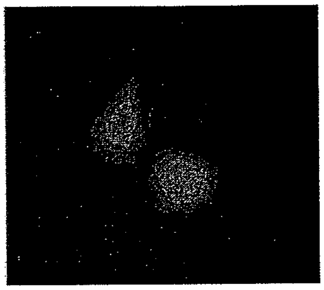
Figure 12D:
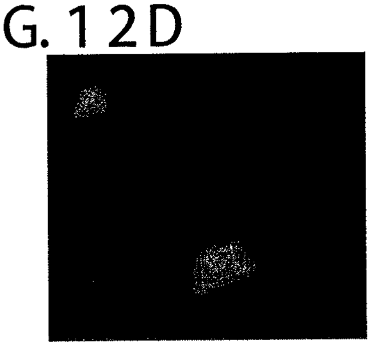
Figure 12E:
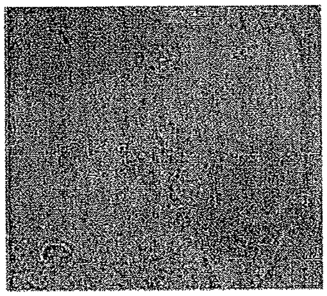
Figure 12F:
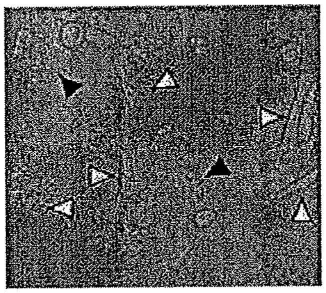
Figure 12G:
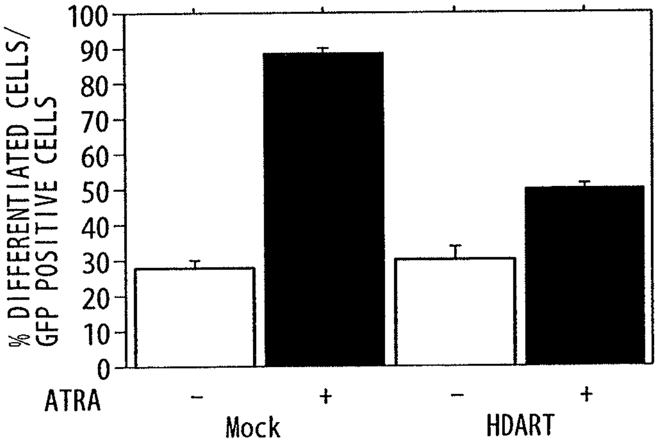

Most of the vacant vector-introduced cells were, due to the ATRA treatment, differentiated into muscle tissue as shown by the appearance of the myotubular cytomegalic cells (FIG. 12B, FIG. 12G). With the vacant vector-introduced cells, the degrees of change in phenotype caused by the ATRA treatment were same for both positive and negative cells. However, with the HDART-introduced cells, little change in the phenotype appeared even when the GFP positive cells were subjected to ATRA treatment (black arrow in FIG. 12D, FIG. 12G). On the other hand, with GFP negative cells, characteristic myotubular cytomegalic cells were observed (white arrow in FIG. 12F). These results show that the expression of HDART represses the differentiation with retinoic acid. The results are consistent with those results of repressing the transcription activity RAR with HDART in the reporter analyses. These results reveal that HDART serves at least as a co-repressor of physiological transcription by retinoic acid receptor.

INDUSTRIAL APPLICABILITY

As stated above, the transcription repressor factor of the invention autonomously represses transcription, particularly, the transcription by nuclear receptors, and thus can be used to act on desired transcription systems for the purpose of repressing transcription of said transcription systems. Moreover, the transcription repressor factor of the invention has the capability of binding to HDAC, and is able to bring about the transcription repressing ability of HDAC via its histone deacetylization activity. Accordingly, the HDAC is recruited by use of the transcription repressor factor of the invention, thereby repressing transcription by the action of the HDAC. This activity of the transcription repressor factor of the invention is applicable to diseases resulting, for example, from increased transcription by nuclear receptors. The transcription repressor of the invention is beneficial as a therapeutic medicine for these diseases.

The dominant negative peptide of the transcription repressor factor functions as a transcription activating factor. Accordingly, this dominant negative peptide can be used to promote the transcription. This dominant negative peptide also acts for transcription of nuclear receptors and, to the contrary, promotes transcription. Hence, the peptide is beneficial as a transcription-promoting substance for nuclear receptors. Especially, the four TPRs segment at the N terminus side of HDART (N4TPR) has a higher transcription activation capability than ATRA for the retinoic acid receptor, and thus, the peptide of the invention can be applied as a therapeutic medicine in place of ATRA or along with ATRA in the treatment of diseases where ATRA is currently employed (e.g. in a differentiation-inducing therapy of malignancies or the like).

The invention claimed is:

1. An isolated DNA molecule comprising a DNA sequence encoding a peptide capable of activating transcription, wherein (A) the peptide comprises the sequence of amino acids 1 to 179 of SEQ ID NO: 2; or (B) the DNA sequence comprises the sequence of nucleotides 37 to 573 of SEQ ID NO: 1.

2. A vector comprising the isolated DNA molecule as set forth in claim 1.

3. A host cell comprising the vector as set forth in claim 2.

4. A host cell comprising the isolated DNA molecule as set forth in claim 1.

5. An isolated DNA molecule comprising a DNA sequence encoding a peptide capable of activating transcription, wherein (A) the peptide comprises an amino acid sequence that is at least 95% identical to the sequence of amino acids 1 to 179 of SEQ ID NO: 2; or (B) the DNA sequence comprises a sequence that is at least 95% identical to the sequence of nucleotides 37 to 573 of SEQ ID NO: 1.

6. A vector comprising the isolated DNA molecule as set forth in claim 5.

7. A host cell comprising the vector as set forth in claim 6.

8. A host cell comprising the isolated DNA molecule as set forth in claim 5.

9. The isolated DNA molecule according to claim 5, wherein (A) the peptide comprises an amino acid sequence that is at least 99% identical to the sequence of amino acids 1 to 179 of SEQ ID NO: 2; or (B) the DNA sequence comprises a sequence that is at least 99% identical to the sequence of nucleotides 37 to 573 of SEQ ID NO: 1.

* * * * *

SEQUENCE LISTING

```
<160> NUMBER OF SEQ ID NOS: 4

<210> SEQ ID NO 1
<211> LENGTH: 2684
<212> TYPE: DNA
<213> ORGANISM: Homo sapiens
<220> FEATURE:
<221> NAME/KEY: CDS
<222> LOCATION: (37)..(2601)

<400> SEQUENCE: 1

agcgcgcgac tctcctgtac ctgggcatcc agaaaa atg gtg gtg atg gcg cga        54
                                        Met Val Val Met Ala Arg
                                        1               5

ctt tcg cgg ccc gag cgg ccg gac ctt gtc ttc gag gaa gag gac ctc       102
Leu Ser Arg Pro Glu Arg Pro Asp Leu Val Phe Glu Glu Glu Asp Leu
            10                  15                  20

ccc tat gag gag gaa atc atg cgg aac caa ttc tct gtc aaa tgc tgg       150
Pro Tyr Glu Glu Glu Ile Met Arg Asn Gln Phe Ser Val Lys Cys Trp
        25                  30                  35

ctt cgc tac atc gag ttc aaa cag ggc gcc ccg aag ccc agg ctc aat       198
Leu Arg Tyr Ile Glu Phe Lys Gln Gly Ala Pro Lys Pro Arg Leu Asn
    40                  45                  50

cag cta tac gag cgg gca ctc aag ctg ctg ccc tgc agc tac aaa ctc       246
Gln Leu Tyr Glu Arg Ala Leu Lys Leu Leu Pro Cys Ser Tyr Lys Leu
55                  60                  65                  70
```

-continued

```
tgg tac cga tac ctg aag gcg cgt cgg gca cag gtg aag cat cgc tgt      294
Trp Tyr Arg Tyr Leu Lys Ala Arg Arg Ala Gln Val Lys His Arg Cys
                75                  80                  85

gtg acc gac cct gcc tat gaa gat gtc aac aac tgt cat gag agg gcc      342
Val Thr Asp Pro Ala Tyr Glu Asp Val Asn Asn Cys His Glu Arg Ala
            90                  95                  100

ttt gtg ttc atg cac aag atg cct cgt ctg tgg cta gat tac tgc cag      390
Phe Val Phe Met His Lys Met Pro Arg Leu Trp Leu Asp Tyr Cys Gln
        105                 110                 115

ttc ctc atg gac cag ggg cgc gtc aca cac acc cgc cgc acc ttc gac      438
Phe Leu Met Asp Gln Gly Arg Val Thr His Thr Arg Arg Thr Phe Asp
    120                 125                 130

cgt gcc ctc cgg gca ctg ccc atc acg cag cac tct cga att tgg ccc      486
Arg Ala Leu Arg Ala Leu Pro Ile Thr Gln His Ser Arg Ile Trp Pro
135                 140                 145                 150

ctg tat ctg cgc ttc ctg cgc tca cac cca ctg cct gag aca gct gtg      534
Leu Tyr Leu Arg Phe Leu Arg Ser His Pro Leu Pro Glu Thr Ala Val
                155                 160                 165

cga ggc tat cgg cgc ttc ctc aag ctg agt cct gag agt gca gag gag      582
Arg Gly Tyr Arg Arg Phe Leu Lys Leu Ser Pro Glu Ser Ala Glu Glu
            170                 175                 180

tac att gag tac ctc aag tca agt gac cgg ctg gat gag gcc gcc cag      630
Tyr Ile Glu Tyr Leu Lys Ser Ser Asp Arg Leu Asp Glu Ala Ala Gln
        185                 190                 195

cgc ctg gcc acc gtg gtg aac gac gag cgt ttc gtg tct aag gcc ggc      678
Arg Leu Ala Thr Val Val Asn Asp Glu Arg Phe Val Ser Lys Ala Gly
    200                 205                 210

aag tcc aac tac cag ctg tgg cac gag ctg tgc gac ctc atc tcc cag      726
Lys Ser Asn Tyr Gln Leu Trp His Glu Leu Cys Asp Leu Ile Ser Gln
215                 220                 225                 230

aat ccg gac aag gta cag tcc ctc aat gtg gac gcc atc atc cgc ggg      774
Asn Pro Asp Lys Val Gln Ser Leu Asn Val Asp Ala Ile Ile Arg Gly
                235                 240                 245

ggc ctc acc cgc ttc acc gac cag ctg ggc aag ctc tgg tgt tct ctc      822
Gly Leu Thr Arg Phe Thr Asp Gln Leu Gly Lys Leu Trp Cys Ser Leu
            250                 255                 260

gcc gac tac tac atc cgc agc ggc cat ttc gag aag gct cgg gac gtg      870
Ala Asp Tyr Tyr Ile Arg Ser Gly His Phe Glu Lys Ala Arg Asp Val
        265                 270                 275

tac gag gag gcc atc cgg aca gtg atg acc gtg cgg gac ttc aca cag      918
Tyr Glu Glu Ala Ile Arg Thr Val Met Thr Val Arg Asp Phe Thr Gln
    280                 285                 290

gtg ttt gac agc tac gcc cag ttc gag gag agc atg atc gct gca aag      966
Val Phe Asp Ser Tyr Ala Gln Phe Glu Glu Ser Met Ile Ala Ala Lys
295                 300                 305                 310

atg gag acc gcc tcg gag ctg ggg cgc gag gag gag gat gat gtg gac     1014
Met Glu Thr Ala Ser Glu Leu Gly Arg Glu Glu Glu Asp Asp Val Asp
                315                 320                 325

ctg gag ctg cgc ctg gcc cgc ttc gag cag ctc atc agc cgg cgg ccc     1062
Leu Glu Leu Arg Leu Ala Arg Phe Glu Gln Leu Ile Ser Arg Arg Pro
            330                 335                 340

ctg ctc ctc aac agc gtc ttg ctg cgc caa aac cca cac cac gtg cac     1110
Leu Leu Leu Asn Ser Val Leu Leu Arg Gln Asn Pro His His Val His
        345                 350                 355

gag tgg cac aag cgt gtc gcc ctg cac cag ggc cgc ccc cgg gag atc     1158
Glu Trp His Lys Arg Val Ala Leu His Gln Gly Arg Pro Arg Glu Ile
    360                 365                 370

atc aac acc tac aca gag gct gtg cag acg gtg gac ccc ttc aag gcc     1206
Ile Asn Thr Tyr Thr Glu Ala Val Gln Thr Val Asp Pro Phe Lys Ala
375                 380                 385                 390
```

```
aca ggc aag ccc cac act ctg tgg gtg gcg ttt gcc aag ttt tat gag     1254
Thr Gly Lys Pro His Thr Leu Trp Val Ala Phe Ala Lys Phe Tyr Glu
                395                 400                 405

gac aac gga cag ctg gac gat gcc cgt gtc atc ctg gag aag gcc acc     1302
Asp Asn Gly Gln Leu Asp Asp Ala Arg Val Ile Leu Glu Lys Ala Thr
            410                 415                 420

aag gtg aac ttc aag cag gtg gat gac ctg gca agc gtg tgg tgt cag     1350
Lys Val Asn Phe Lys Gln Val Asp Asp Leu Ala Ser Val Trp Cys Gln
        425                 430                 435

tgc gga gag ctg gag ctc cga cac gag aac tac gat gag gcc ttg cgg     1398
Cys Gly Glu Leu Glu Leu Arg His Glu Asn Tyr Asp Glu Ala Leu Arg
    440                 445                 450

ctg ctg cga aag gcc acg gcg ctg cct gcc cgc cgg gcc gag tac ttt     1446
Leu Leu Arg Lys Ala Thr Ala Leu Pro Ala Arg Arg Ala Glu Tyr Phe
455                 460                 465                 470

gat ggt tca gag ccc gtg cag aac cgc gtg tac aag tca ctg aag gtc     1494
Asp Gly Ser Glu Pro Val Gln Asn Arg Val Tyr Lys Ser Leu Lys Val
                475                 480                 485

tgg tcc atg ctc gcc gac ctg gag gag agc ctc ggc acc ttc cag tcc     1542
Trp Ser Met Leu Ala Asp Leu Glu Glu Ser Leu Gly Thr Phe Gln Ser
            490                 495                 500

acc aag gcc gtg tac gac cgc atc ctg gac ctg cgt atc gca aca ccc     1590
Thr Lys Ala Val Tyr Asp Arg Ile Leu Asp Leu Arg Ile Ala Thr Pro
        505                 510                 515

cag atc gtc atc aac tat gcc atg ttc ctg gag gag cac aag tac ttc     1638
Gln Ile Val Ile Asn Tyr Ala Met Phe Leu Glu Glu His Lys Tyr Phe
    520                 525                 530

gag gag agc ttc aag gcg tac gag cgc ggc atc tcg ctg ttc aag tgg     1686
Glu Glu Ser Phe Lys Ala Tyr Glu Arg Gly Ile Ser Leu Phe Lys Trp
535                 540                 545                 550

ccc aac gtg tcc gac atc tgg agc acc tac ctg acc aaa ttc att gcc     1734
Pro Asn Val Ser Asp Ile Trp Ser Thr Tyr Leu Thr Lys Phe Ile Ala
                555                 560                 565

cgc tat ggg ggc cgc aag ctg gag cgg gca cgg gac ctg ttt gaa cag     1782
Arg Tyr Gly Gly Arg Lys Leu Glu Arg Ala Arg Asp Leu Phe Glu Gln
            570                 575                 580

gct ctg gac ggc tgc ccc cca aaa tat gcc aag acc ttg tac ctg ctg     1830
Ala Leu Asp Gly Cys Pro Pro Lys Tyr Ala Lys Thr Leu Tyr Leu Leu
        585                 590                 595

tac gca cag ctg gag gag gag tgg ggc ctg gcc cgg cat gcc atg gcc     1878
Tyr Ala Gln Leu Glu Glu Glu Trp Gly Leu Ala Arg His Ala Met Ala
    600                 605                 610

gtg tac gag cgt gcc acc agg gcc gtg gag ccc gcc cag cag tat gac     1926
Val Tyr Glu Arg Ala Thr Arg Ala Val Glu Pro Ala Gln Gln Tyr Asp
615                 620                 625                 630

atg ttc aac atc tac atc aag cgg gcg gcc gag atc tat ggg gtc acc     1974
Met Phe Asn Ile Tyr Ile Lys Arg Ala Ala Glu Ile Tyr Gly Val Thr
                635                 640                 645

cac acc cgc ggc atc tac cag aag gcc att gag gtg ctg tcg gac gag     2022
His Thr Arg Gly Ile Tyr Gln Lys Ala Ile Glu Val Leu Ser Asp Glu
            650                 655                 660

cac gcg cgt gag atg tgc ctg cgg ttt gca gac atg gag tgc aag ctc     2070
His Ala Arg Glu Met Cys Leu Arg Phe Ala Asp Met Glu Cys Lys Leu
        665                 670                 675

ggg gag att gac cgc gcc cgg gcc atc tac agc ttc tgc tcc cag atc     2118
Gly Glu Ile Asp Arg Ala Arg Ala Ile Tyr Ser Phe Cys Ser Gln Ile
    680                 685                 690

tgt gac ccc cgg acg acc ggc gcg ttc tgg cag acg tgg aag gac ttt     2166
Cys Asp Pro Arg Thr Thr Gly Ala Phe Trp Gln Thr Trp Lys Asp Phe
```

-continued

```
695                 700                 705                 710

gag gtc cgg cat ggc aat gag gac acc atc aag gaa atg ctg cgt atc      2214
Glu Val Arg His Gly Asn Glu Asp Thr Ile Lys Glu Met Leu Arg Ile
                715                 720                 725

cgg cgc agc gtg cag gcc acg tac aac acg cag gtc aac ttc atg gcc      2262
Arg Arg Ser Val Gln Ala Thr Tyr Asn Thr Gln Val Asn Phe Met Ala
            730                 735                 740

tcg cag atg ctc aag gtc tcg ggc agt gcc acg ggc acc gtg tct gac      2310
Ser Gln Met Leu Lys Val Ser Gly Ser Ala Thr Gly Thr Val Ser Asp
        745                 750                 755

ctg gcc cct ggg cag agt ggc atg gac gac atg aag ctg ctg gaa cag      2358
Leu Ala Pro Gly Gln Ser Gly Met Asp Asp Met Lys Leu Leu Glu Gln
    760                 765                 770

cgg gca gag cag ctg gcg gct gag gcg gag cgt gac cag ccc ttg cgc      2406
Arg Ala Glu Gln Leu Ala Ala Glu Ala Glu Arg Asp Gln Pro Leu Arg
775                 780                 785                 790

gcc cag agc aag atc ctg ttc gtg agg agt gac gcc tcc cgg gag gag      2454
Ala Gln Ser Lys Ile Leu Phe Val Arg Ser Asp Ala Ser Arg Glu Glu
                795                 800                 805

ctg gca gag ctg gca cag cag gtc aac ccc gag gag atc cag ctg ggc      2502
Leu Ala Glu Leu Ala Gln Gln Val Asn Pro Glu Glu Ile Gln Leu Gly
            810                 815                 820

gag gac gag gac gag gac gag atg gac ctg gag ccc aac gag gtt cgg      2550
Glu Asp Glu Asp Glu Asp Glu Met Asp Leu Glu Pro Asn Glu Val Arg
        825                 830                 835

ctg gag cag cag agc gtg cca gcc gca gtg ttt ggg agc ctg aag gaa      2598
Leu Glu Gln Gln Ser Val Pro Ala Ala Val Phe Gly Ser Leu Lys Glu
    840                 845                 850

gac tgacccgtcc ctcccccatc cccccctcccc accccctccc caatacagct          2651
Asp
855

acgtttgtac aaaaaaaaaa aaaaaaaaaa aaa                                 2684


<210> SEQ ID NO 2
<211> LENGTH: 855
<212> TYPE: PRT
<213> ORGANISM: Homo sapiens

<400> SEQUENCE: 2

Met Val Val Met Ala Arg Leu Ser Arg Pro Glu Arg Pro Asp Leu Val
1               5                   10                  15

Phe Glu Glu Glu Asp Leu Pro Tyr Glu Glu Glu Ile Met Arg Asn Gln
            20                  25                  30

Phe Ser Val Lys Cys Trp Leu Arg Tyr Ile Glu Phe Lys Gln Gly Ala
        35                  40                  45

Pro Lys Pro Arg Leu Asn Gln Leu Tyr Glu Arg Ala Leu Lys Leu Leu
    50                  55                  60

Pro Cys Ser Tyr Lys Leu Trp Tyr Arg Tyr Leu Lys Ala Arg Arg Ala
65                  70                  75                  80

Gln Val Lys His Arg Cys Val Thr Asp Pro Ala Tyr Glu Asp Val Asn
                85                  90                  95

Asn Cys His Glu Arg Ala Phe Val Phe Met His Lys Met Pro Arg Leu
            100                 105                 110

Trp Leu Asp Tyr Cys Gln Phe Leu Met Asp Gln Gly Arg Val Thr His
        115                 120                 125

Thr Arg Arg Thr Phe Asp Arg Ala Leu Arg Ala Leu Pro Ile Thr Gln
    130                 135                 140
```

-continued

```
His Ser Arg Ile Trp Pro Leu Tyr Leu Arg Phe Leu Arg Ser His Pro
145                 150                 155                 160

Leu Pro Glu Thr Ala Val Arg Gly Tyr Arg Arg Phe Leu Lys Leu Ser
                165                 170                 175

Pro Glu Ser Ala Glu Glu Tyr Ile Glu Tyr Leu Lys Ser Ser Asp Arg
            180                 185                 190

Leu Asp Glu Ala Ala Gln Arg Leu Ala Thr Val Val Asn Asp Glu Arg
        195                 200                 205

Phe Val Ser Lys Ala Gly Lys Ser Asn Tyr Gln Leu Trp His Glu Leu
    210                 215                 220

Cys Asp Leu Ile Ser Gln Asn Pro Asp Lys Val Gln Ser Leu Asn Val
225                 230                 235                 240

Asp Ala Ile Ile Arg Gly Gly Leu Thr Arg Phe Thr Asp Gln Leu Gly
                245                 250                 255

Lys Leu Trp Cys Ser Leu Ala Asp Tyr Tyr Ile Arg Ser Gly His Phe
            260                 265                 270

Glu Lys Ala Arg Asp Val Tyr Glu Glu Ala Ile Arg Thr Val Met Thr
        275                 280                 285

Val Arg Asp Phe Thr Gln Val Phe Asp Ser Tyr Ala Gln Phe Glu Glu
    290                 295                 300

Ser Met Ile Ala Ala Lys Met Glu Thr Ala Ser Glu Leu Gly Arg Glu
305                 310                 315                 320

Glu Glu Asp Asp Val Asp Leu Glu Leu Arg Leu Ala Arg Phe Glu Gln
                325                 330                 335

Leu Ile Ser Arg Arg Pro Leu Leu Leu Asn Ser Val Leu Leu Arg Gln
            340                 345                 350

Asn Pro His His Val His Glu Trp His Lys Arg Val Ala Leu His Gln
        355                 360                 365

Gly Arg Pro Arg Glu Ile Ile Asn Thr Tyr Thr Glu Ala Val Gln Thr
    370                 375                 380

Val Asp Pro Phe Lys Ala Thr Gly Lys Pro His Thr Leu Trp Val Ala
385                 390                 395                 400

Phe Ala Lys Phe Tyr Glu Asp Asn Gly Gln Leu Asp Asp Ala Arg Val
                405                 410                 415

Ile Leu Glu Lys Ala Thr Lys Val Asn Phe Lys Gln Val Asp Asp Leu
            420                 425                 430

Ala Ser Val Trp Cys Gln Cys Gly Glu Leu Glu Leu Arg His Glu Asn
        435                 440                 445

Tyr Asp Glu Ala Leu Arg Leu Leu Arg Lys Ala Thr Ala Leu Pro Ala
    450                 455                 460

Arg Arg Ala Glu Tyr Phe Asp Gly Ser Glu Pro Val Gln Asn Arg Val
465                 470                 475                 480

Tyr Lys Ser Leu Lys Val Trp Ser Met Leu Ala Asp Leu Glu Glu Ser
                485                 490                 495

Leu Gly Thr Phe Gln Ser Thr Lys Ala Val Tyr Asp Arg Ile Leu Asp
            500                 505                 510

Leu Arg Ile Ala Thr Pro Gln Ile Val Ile Asn Tyr Ala Met Phe Leu
        515                 520                 525

Glu Glu His Lys Tyr Phe Glu Glu Ser Phe Lys Ala Tyr Glu Arg Gly
    530                 535                 540

Ile Ser Leu Phe Lys Trp Pro Asn Val Ser Asp Ile Trp Ser Thr Tyr
545                 550                 555                 560

Leu Thr Lys Phe Ile Ala Arg Tyr Gly Gly Arg Lys Leu Glu Arg Ala
```

-continued

```
                565                 570                 575

Arg Asp Leu Phe Glu Gln Ala Leu Asp Gly Cys Pro Pro Lys Tyr Ala
            580                 585                 590

Lys Thr Leu Tyr Leu Leu Tyr Ala Gln Leu Glu Glu Glu Trp Gly Leu
        595                 600                 605

Ala Arg His Ala Met Ala Val Tyr Glu Arg Ala Thr Arg Ala Val Glu
    610                 615                 620

Pro Ala Gln Gln Tyr Asp Met Phe Asn Ile Tyr Ile Lys Arg Ala Ala
625                 630                 635                 640

Glu Ile Tyr Gly Val Thr His Thr Arg Gly Ile Tyr Gln Lys Ala Ile
                645                 650                 655

Glu Val Leu Ser Asp Glu His Ala Arg Glu Met Cys Leu Arg Phe Ala
            660                 665                 670

Asp Met Glu Cys Lys Leu Gly Glu Ile Asp Arg Ala Arg Ala Ile Tyr
        675                 680                 685

Ser Phe Cys Ser Gln Ile Cys Asp Pro Arg Thr Thr Gly Ala Phe Trp
    690                 695                 700

Gln Thr Trp Lys Asp Phe Glu Val Arg His Gly Asn Glu Asp Thr Ile
705                 710                 715                 720

Lys Glu Met Leu Arg Ile Arg Arg Ser Val Gln Ala Thr Tyr Asn Thr
                725                 730                 735

Gln Val Asn Phe Met Ala Ser Gln Met Leu Lys Val Ser Gly Ser Ala
            740                 745                 750

Thr Gly Thr Val Ser Asp Leu Ala Pro Gly Gln Ser Gly Met Asp Asp
        755                 760                 765

Met Lys Leu Leu Glu Gln Arg Ala Glu Gln Leu Ala Ala Glu Ala Glu
    770                 775                 780

Arg Asp Gln Pro Leu Arg Ala Gln Ser Lys Ile Leu Phe Val Arg Ser
785                 790                 795                 800

Asp Ala Ser Arg Glu Glu Leu Ala Glu Leu Ala Gln Gln Val Asn Pro
                805                 810                 815

Glu Glu Ile Gln Leu Gly Glu Asp Glu Asp Glu Asp Glu Met Asp Leu
            820                 825                 830

Glu Pro Asn Glu Val Arg Leu Glu Gln Gln Ser Val Pro Ala Ala Val
        835                 840                 845

Phe Gly Ser Leu Lys Glu Asp
    850                 855


<210> SEQ ID NO 3
<211> LENGTH: 518
<212> TYPE: PRT
<213> ORGANISM: Homo sapiens

<400> SEQUENCE: 3

Leu Ala Asp Tyr Tyr Ile Arg Ser Gly His Phe Glu Lys Ala Arg Asp
1               5                   10                  15

Val Tyr Glu Glu Ala Ile Arg Thr Val Met Thr Val Arg Asp Phe Thr
            20                  25                  30

Gln Val Phe Asp Ser Tyr Ala Gln Phe Glu Glu Ser Met Ile Ala Ala
        35                  40                  45

Lys Met Glu Thr Ala Ser Glu Leu Gly Arg Glu Glu Glu Asp Asp Val
    50                  55                  60

Asp Leu Glu Leu Arg Leu Ala Arg Phe Glu Gln Leu Ile Ser Arg Arg
65                  70                  75                  80
```

-continued

```
Pro Leu Leu Leu Asn Ser Val Leu Leu Arg Gln Asn Pro His His Val
                85                  90                  95

His Glu Trp His Lys Arg Val Ala Leu His Gln Gly Arg Pro Arg Glu
            100                 105                 110

Ile Ile Asn Thr Tyr Thr Glu Ala Val Gln Thr Val Asp Pro Phe Lys
        115                 120                 125

Ala Thr Gly Lys Pro His Thr Leu Trp Val Ala Phe Ala Lys Phe Tyr
    130                 135                 140

Glu Asp Asn Gly Gln Leu Asp Asp Ala Arg Val Ile Leu Glu Lys Ala
145                 150                 155                 160

Thr Lys Val Asn Phe Lys Gln Val Asp Asp Leu Ala Ser Val Trp Cys
                165                 170                 175

Gln Cys Gly Glu Leu Glu Leu Arg His Glu Asn Tyr Asp Glu Ala Leu
            180                 185                 190

Arg Leu Leu Arg Lys Ala Thr Ala Leu Pro Ala Arg Arg Ala Glu Tyr
        195                 200                 205

Phe Asp Gly Ser Glu Pro Val Gln Asn Arg Val Tyr Lys Ser Leu Lys
    210                 215                 220

Val Trp Ser Met Leu Ala Asp Leu Glu Glu Ser Leu Gly Thr Phe Gln
225                 230                 235                 240

Ser Thr Lys Ala Val Tyr Asp Arg Ile Leu Asp Leu Arg Ile Ala Thr
                245                 250                 255

Pro Gln Ile Val Ile Asn Tyr Ala Met Phe Leu Glu Glu His Lys Tyr
            260                 265                 270

Phe Glu Glu Ser Phe Lys Ala Tyr Glu Arg Gly Ile Ser Leu Phe Lys
        275                 280                 285

Trp Pro Asn Val Ser Asp Ile Trp Ser Thr Tyr Leu Thr Lys Phe Ile
    290                 295                 300

Ala Arg Tyr Gly Gly Arg Lys Leu Glu Arg Ala Arg Asp Leu Phe Glu
305                 310                 315                 320

Gln Ala Leu Asp Gly Cys Pro Pro Lys Tyr Ala Lys Thr Leu Tyr Leu
                325                 330                 335

Leu Tyr Ala Gln Leu Glu Glu Glu Trp Gly Leu Ala Arg His Ala Met
            340                 345                 350

Ala Val Tyr Glu Arg Ala Thr Arg Ala Val Glu Pro Ala Gln Gln Tyr
        355                 360                 365

Asp Met Phe Asn Ile Tyr Ile Lys Arg Ala Ala Glu Ile Tyr Gly Val
    370                 375                 380

Thr His Thr Arg Gly Ile Tyr Gln Lys Ala Ile Glu Val Leu Ser Asp
385                 390                 395                 400

Glu His Ala Arg Glu Met Cys Leu Arg Phe Ala Asp Met Glu Cys Lys
                405                 410                 415

Leu Gly Glu Ile Asp Arg Ala Arg Ala Ile Tyr Ser Phe Cys Ser Gln
            420                 425                 430

Ile Cys Asp Pro Arg Thr Thr Gly Ala Phe Trp Gln Thr Trp Lys Asp
        435                 440                 445

Phe Glu Val Arg His Gly Asn Glu Asp Thr Ile Lys Glu Met Leu Arg
    450                 455                 460

Ile Arg Arg Ser Val Gln Ala Thr Tyr Asn Thr Gln Val Asn Phe Met
465                 470                 475                 480

Ala Ser Gln Met Leu Lys Val Ser Gly Ser Ala Thr Gly Thr Val Ser
                485                 490                 495

Asp Leu Ala Pro Gly Gln Ser Gly Met Asp Asp Met Lys Leu Leu Glu
```

```
            500                 505                 510

Gln Arg Ala Glu Gln Leu
        515


<210> SEQ ID NO 4
<211> LENGTH: 533
<212> TYPE: PRT
<213> ORGANISM: Homo sapiens

<400> SEQUENCE: 4

Leu Asn Asp Tyr Lys Leu Arg Lys Arg Lys Thr Phe Glu Asp Asn Ile
1               5                   10                  15

Arg Lys Asn Arg Thr Val Ile Ser Asn Trp Ile Lys Tyr Ala Gln Trp
            20                  25                  30

Glu Glu Ser Leu Lys Glu Ile Gln Arg Ala Arg Ser Ile Tyr Glu Arg
        35                  40                  45

Ala Leu Asp Val Asp Tyr Arg Asn Ile Thr Leu Trp Leu Lys Tyr Ala
    50                  55                  60

Glu Met Glu Met Lys Asn Arg Gln Val Asn His Ala Arg Asn Ile Trp
65                  70                  75                  80

Asp Arg Ala Ile Thr Thr Leu Pro Arg Val Asn Gln Phe Trp Tyr Lys
                85                  90                  95

Tyr Thr Tyr Met Glu Glu Met Leu Gly Asn Val Ala Gly Ala Arg Gln
            100                 105                 110

Val Phe Glu Arg Trp Met Glu Trp Gln Pro Glu Glu Gln Ala Trp His
        115                 120                 125

Ser Tyr Ile Asn Phe Glu Leu Arg Tyr Lys Glu Val Asp Arg Ala Arg
    130                 135                 140

Thr Ile Tyr Glu Arg Phe Val Leu Val His Pro Asp Val Lys Asn Trp
145                 150                 155                 160

Ile Lys Tyr Ala Arg Phe Glu Glu Lys His Ala Tyr Phe Ala His Ala
                165                 170                 175

Arg Lys Val Tyr Glu Arg Ala Val Glu Phe Phe Gly Asp Glu His Met
            180                 185                 190

Asp Glu His Leu Tyr Val Ala Phe Ala Lys Phe Glu Glu Asn Gln Lys
        195                 200                 205

Glu Phe Glu Arg Val Arg Val Ile Tyr Lys Tyr Ala Leu Asp Arg Ile
    210                 215                 220

Ser Lys Gln Asp Ala Gln Glu Leu Phe Lys Asn Tyr Thr Ile Phe Glu
225                 230                 235                 240

Lys Lys Phe Gly Asp Arg Arg Gly Ile Glu Asp Ile Ile Val Ser Lys
                245                 250                 255

Arg Arg Phe Gln Tyr Glu Glu Glu Val Lys Ala Asn Pro His Asn Tyr
            260                 265                 270

Asp Ala Trp Phe Asp Tyr Leu Arg Leu Val Glu Ser Asp Ala Glu Ala
        275                 280                 285

Glu Ala Val Arg Glu Val Tyr Glu Arg Ala Ile Ala Asn Val Pro Pro
    290                 295                 300

Ile Gln Glu Lys Arg His Trp Lys Arg Tyr Ile Tyr Leu Trp Ile Asn
305                 310                 315                 320

Tyr Ala Leu Tyr Glu Glu Leu Glu Ala Lys Asp Pro Glu Arg Thr Arg
                325                 330                 335

Gln Val Tyr Gln Ala Ser Leu Glu Leu Ile Pro His Lys Lys Phe Thr
            340                 345                 350
```

-continued

| | | | | | | | | | | | | | | | |
|---|---|---|---|---|---|---|---|---|---|---|---|---|---|---|---|
| Phe | Ala | Lys | Met | Trp | Ile | Leu | Tyr | Ala | Gln | Phe | Glu | Ile | Arg | Gln | Lys |
| | | 355 | | | | | 360 | | | | | 365 | | | |
| Asn | Leu | Ser | Leu | Ala | Arg | Arg | Ala | Leu | Gly | Thr | Ser | Ile | Gly | Lys | Cys |
| | 370 | | | | | 375 | | | | | 380 | | | | |
| Pro | Lys | Asn | Lys | Leu | Phe | Lys | Val | Tyr | Ile | Glu | Leu | Glu | Leu | Gln | Leu |
| 385 | | | | | 390 | | | | | 395 | | | | | 400 |
| Arg | Glu | Phe | Asp | Arg | Cys | Arg | Lys | Leu | Tyr | Glu | Lys | Phe | Leu | Glu | Phe |
| | | | | 405 | | | | | 410 | | | | | 415 | |
| Gly | Pro | Glu | Asn | Cys | Thr | Ser | Trp | Ile | Lys | Phe | Ala | Glu | Leu | Glu | Thr |
| | | | 420 | | | | | 425 | | | | | 430 | | |
| Ile | Leu | Gly | Asp | Ile | Asp | Arg | Ala | Arg | Ala | Ile | Tyr | Glu | Leu | Ala | Ile |
| | | 435 | | | | | 440 | | | | | 445 | | | |
| Ser | Gln | Pro | Arg | Leu | Asp | Met | Pro | Glu | Val | Leu | Trp | Lys | Ser | Tyr | Ile |
| | 450 | | | | | 455 | | | | | 460 | | | | |
| Asp | Phe | Glu | Ile | Glu | Gln | Glu | Glu | Thr | Glu | Arg | Thr | Arg | Asn | Leu | Tyr |
| 465 | | | | | 470 | | | | | 475 | | | | | 480 |
| Arg | Arg | Leu | Leu | Gln | Arg | Thr | Gln | His | Val | Lys | Val | Trp | Ile | Ser | Phe |
| | | | | 485 | | | | | 490 | | | | | 495 | |
| Ala | Gln | Phe | Glu | Leu | Ser | Ser | Gly | Lys | Glu | Gly | Ser | Leu | Thr | Lys | Cys |
| | | | 500 | | | | | 505 | | | | | 510 | | |
| Arg | Gln | Ile | Tyr | Glu | Glu | Ala | Asn | Lys | Thr | Met | Arg | Asn | Cys | Glu | Glu |
| | | 515 | | | | | 520 | | | | | 525 | | | |
| Lys | Glu | Glu | Arg | Leu | | | | | | | | | | | |
| | 530 | | | | | | | | | | | | | | |